(12) United States Patent
Kietzmann

(10) Patent No.: US 11,724,021 B2
(45) Date of Patent: Aug. 15, 2023

(54) PACKAGING ASSEMBLY

(71) Applicant: SANOFI, Paris (FR)

(72) Inventor: Hardy Kietzmann, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 17/088,269

(22) Filed: Nov. 3, 2020

(65) Prior Publication Data

US 2021/0046239 A1 Feb. 18, 2021

Related U.S. Application Data

(63) Continuation of application No. 16/487,013, filed as application No. PCT/EP2018/054323 on Feb. 22, 2018, now Pat. No. 11,565,034.

(30) Foreign Application Priority Data

Feb. 24, 2017 (EP) ..................................... 17305210

(51) Int. Cl.
*G16H 20/17* (2018.01)
*A61M 5/00* (2006.01)
(Continued)

(52) U.S. Cl.
CPC ............. *A61M 5/002* (2013.01); *G09G 3/04* (2013.01); *G16H 20/13* (2018.01); *G16H 20/17* (2018.01);
(Continued)

(58) Field of Classification Search
CPC ................... A61M 5/002; A61M 5/20; A61M 2205/3306; A61M 2205/502; A61M 2205/52; A61M 2205/581; A61M 2205/583; A61M 2205/587; A61M 2205/6054; A61M 2205/6072;
(Continued)

(56) References Cited

U.S. PATENT DOCUMENTS 2,698,155 A 12/1954 Bowman
4,572,403 A 2/1986 Benaroya
(Continued)

FOREIGN PATENT DOCUMENTS

CN 2568179 8/2003
CN 1630604 6/2005
(Continued)

OTHER PUBLICATIONS

PCT International Preliminary Report on Patentability in International Appln. No. PCT/EP2016/079038, dated Jun. 5, 2018, 7 pages.
(Continued)

*Primary Examiner* — Hai Phan
*Assistant Examiner* — Anthony D Afrifa-Kyei
(74) *Attorney, Agent, or Firm* — Fish & Richardson P.C.

(57) ABSTRACT

A packaging assembly comprises a case configured to at least partially contain a plurality of injection devices for delivering a medicament; and a sensor arrangement comprising at least one device sensor; wherein the at least one device sensor is configured to detect one or more injection devices contained in the case, and to output a signal according to a result of the detection.

17 Claims, 17 Drawing Sheets

(51) Int. Cl.
*G16H 20/13* (2018.01)
*G09G 3/04* (2006.01)
*A61M 5/20* (2006.01)

(52) U.S. Cl.
CPC ....... *A61M 5/20* (2013.01); *A61M 2205/3306* (2013.01); *A61M 2205/502* (2013.01); *A61M 2205/52* (2013.01); *A61M 2205/581* (2013.01); *A61M 2205/583* (2013.01); *A61M 2205/587* (2013.01); *A61M 2205/6054* (2013.01); *A61M 2205/6072* (2013.01); *A61M 2205/8206* (2013.01); *G09G 2380/08* (2013.01)

(58) Field of Classification Search
CPC ............ A61M 2205/8206; A61M 5/00; A61M 5/178; A61M 2005/2006; A61M 2005/2026; A61M 2005/206; A61M 2005/2073; A61M 2005/2086; A61M 2005/2093; A61M 5/2033; A61M 5/204; A61M 5/2046; A61M 5/2053; A61M 5/2066; A61M 2005/3125; A61M 2205/50; A61M 5/28; A61M 5/3129; G16H 20/17; G16H 20/13; G09G 3/04; G09G 2380/08; A61J 7/0436; G04B 25/06; G04F 1/005

See application file for complete search history.

(56) References Cited

U.S. PATENT DOCUMENTS

| | | | |
|---|---|---|---|
| 4,903,832 | A | 2/1990 | Stewart |
| 5,522,503 | A | 6/1996 | Halbich |
| 5,915,558 | A | 6/1999 | Girvetz |
| 5,970,974 | A | 10/1999 | Van der Linden et al. |
| 6,056,118 | A | 5/2000 | Hargus et al. |
| 6,464,506 | B1 | 10/2002 | Dickerson |
| 6,595,362 | B2 | 7/2003 | Penney et al. |
| 6,955,259 | B1 | 10/2005 | Jesse |
| 7,434,686 | B2 | 10/2008 | Prindle |
| 7,522,477 | B1* | 4/2009 | Sheldon ................. G04G 11/00 368/10 |
| 8,544,645 | B2 | 10/2013 | Edwards et al. |
| 8,584,486 | B1 | 11/2013 | Allard et al. |
| 9,311,452 | B2 | 4/2016 | Dickie et al. |
| 10,398,524 | B2 | 9/2019 | Denny et al. |
| 10,869,962 | B2 | 12/2020 | Kietzmann et al. |
| 11,103,632 | B2 | 8/2021 | Kietzmann et al. |
| 11,103,633 | B2 | 8/2021 | Kietzmann et al. |
| 11,278,660 | B2 | 3/2022 | Kietzmann et al. |
| 11,369,732 | B2 | 6/2022 | Keitzmann |
| 2002/0050462 | A1 | 5/2002 | Penney et al. |
| 2002/0158058 | A1 | 10/2002 | Faries et al. |
| 2004/0069667 | A1 | 4/2004 | Tomellini et al. |
| 2005/0256388 | A1 | 11/2005 | Susi |
| 2007/0214812 | A1 | 9/2007 | Wagner et al. |
| 2007/0215782 | A1 | 9/2007 | Phung et al. |
| 2007/0246396 | A1* | 10/2007 | Brollier ................. A61J 7/0481 206/534 |
| 2008/0306443 | A1 | 12/2008 | Neer et al. |
| 2009/0115598 | A1 | 5/2009 | Carlson |
| 2009/0134181 | A1 | 5/2009 | Wachman et al. |
| 2011/0218502 | A1 | 9/2011 | Iio et al. |
| 2012/0232520 | A1 | 9/2012 | Sloan et al. |
| 2013/0002795 | A1 | 1/2013 | Shavelsky et al. |
| 2013/0211323 | A1 | 8/2013 | Lee |
| 2013/0289536 | A1 | 10/2013 | Croizat et al. |
| 2014/0018733 | A1* | 1/2014 | Sjolund ................. A61M 5/24 604/111 |
| 2014/0018744 | A1* | 1/2014 | Holmqvist .......... A61M 5/3257 604/192 |
| 2014/0155827 | A1 | 6/2014 | Ostrander et al. |
| 2014/0252927 | A1 | 9/2014 | Denny et al. |
| 2014/0350720 | A1 | 11/2014 | Lehmann et al. |
| 2015/0014210 | A1 | 1/2015 | Priebe et al. |
| 2015/0048100 | A1 | 2/2015 | Dickie et al. |
| 2015/0196711 | A1 | 7/2015 | Edwards et al. |
| 2015/0251839 | A1 | 9/2015 | Denny et al. |
| 2015/0283341 | A1 | 10/2015 | Adams et al. |
| 2015/0317455 | A1 | 11/2015 | Lehmann et al. |
| 2015/0378314 | A1 | 12/2015 | Nakabayashi |
| 2016/0129182 | A1 | 5/2016 | Schuster et al. |
| 2016/0162832 | A1* | 6/2016 | Thompson ......... G06Q 10/0832 705/332 |
| 2016/0199592 | A1 | 7/2016 | Eggert et al. |
| 2016/0232877 | A1 | 8/2016 | Cho et al. |
| 2016/0243318 | A1 | 8/2016 | Despa et al. |
| 2017/0056605 | A1 | 3/2017 | Kondo et al. |
| 2017/0087059 | A1 | 3/2017 | Rodriguez et al. |
| 2017/0224588 | A1* | 8/2017 | Kitson ................. A61J 7/0418 |
| 2017/0368260 | A1 | 12/2017 | McCullough et al. |
| 2018/0015218 | A1 | 1/2018 | Welsch |
| 2018/0236181 | A1 | 8/2018 | Marlin et al. |
| 2019/0030329 | A1* | 1/2019 | Hannaman ........ A61M 5/31568 |
| 2021/0060235 | A1 | 3/2021 | Kietzmann et al. |
| 2021/0353852 | A1 | 11/2021 | Kietzmann et al. |
| 2022/0296805 | A1 | 9/2022 | Keitzmann |

FOREIGN PATENT DOCUMENTS

| | | |
|---|---|---|
| CN | 2744339 | 12/2005 |
| CN | 1871046 | 11/2006 |
| CN | 101073533 | 11/2007 |
| CN | 101116077 | 1/2008 |
| CN | 101152620 | 4/2008 |
| CN | 101318037 | 12/2008 |
| CN | 101384237 | 3/2009 |
| CN | 101405749 | 4/2009 |
| CN | 201352126 | 11/2009 |
| CN | 201664175 | 12/2010 |
| CN | 201829032 | 5/2011 |
| CN | 201877103 | 6/2011 |
| CN | 102202703 | 9/2011 |
| CN | 201979271 | 9/2011 |
| CN | 102542176 | 7/2012 |
| CN | 202287671 | 7/2012 |
| CN | 202311770 | 7/2012 |
| CN | 202426229 | 9/2012 |
| CN | 102770170 | 11/2012 |
| CN | 103380059 | 10/2013 |
| CN | 103619378 | 3/2014 |
| CN | 203634510 | 6/2014 |
| CN | 104055678 | 9/2014 |
| CN | 203970030 | 12/2014 |
| CN | 204050542 | 12/2014 |
| CN | 104363940 | 2/2015 |
| CN | 104491951 | 4/2015 |
| CN | 204351461 | 5/2015 |
| CN | 204467263 | 7/2015 |
| CN | 104870032 | 8/2015 |
| CN | 104955435 | 9/2015 |
| CN | 104956416 | 9/2015 |
| CN | 204766326 | 11/2015 |
| CN | 204890775 | 12/2015 |
| CN | 105307717 | 2/2016 |
| CN | 205041890 | 2/2016 |
| CN | 205098506 | 3/2016 |
| CN | 205872707 | 1/2017 |
| DE | 20201026 | 4/2002 |
| DE | 10132869 | 10/2002 |
| EP | 2119423 | 11/2009 |
| EP | 2357013 | 8/2011 |
| EP | 3010660 | 4/2016 |
| EP | 3103493 | 12/2016 |
| EP | 3449575 | 3/2019 |
| GB | 2520054 | 5/2015 |
| GB | 2520181 | 5/2015 |
| JP | S51-93401 | 7/1976 |
| JP | S61-055792 U | 4/1986 |
| JP | H06-511183 | 12/1994 |
| JP | H10-033639 | 2/1998 |
| JP | 2001-503302 | 3/2001 |
| JP | 2002-504397 | 2/2002 |

(56) References Cited

FOREIGN PATENT DOCUMENTS

| | | |
|---|---|---|
| JP | 2007-510469 | 4/2007 |
| JP | 2008-114008 | 5/2008 |
| JP | 101912641 | 12/2010 |
| JP | 2012-217802 | 11/2012 |
| JP | 3189723 U | 3/2014 |
| JP | 2014-079483 | 5/2014 |
| JP | 2014-111173 | 6/2014 |
| JP | 2014-126231 | 7/2014 |
| JP | 2015-531653 | 11/2015 |
| JP | 2016-518879 | 6/2016 |
| JP | 2016-529016 | 9/2016 |
| KR | 10-1564249 | 11/2015 |
| WO | WO 1994/004966 | 3/1994 |
| WO | WO 1998/019647 | 5/1998 |
| WO | WO 1999/043283 | 9/1999 |
| WO | WO 2001/087739 | 11/2001 |
| WO | WO 2003/062091 | 7/2003 |
| WO | WO 2005/046559 | 5/2005 |
| WO | WO 2006/086735 | 8/2006 |
| WO | WO 2007/082543 | 7/2007 |
| WO | WO 2007/107562 | 9/2007 |
| WO | WO 2007/126851 | 11/2007 |
| WO | WO 2010/055608 | 5/2010 |
| WO | WO 2011/054000 | 5/2011 |
| WO | WO 2011/070329 | 6/2011 |
| WO | WO 2011/080092 | 7/2011 |
| WO | WO 2012/112631 | 8/2012 |
| WO | WO 2012/145752 | 10/2012 |
| WO | WO 2013/025520 | 2/2013 |
| WO | WO 2013/050342 | 4/2013 |
| WO | WO 2013/120776 | 8/2013 |
| WO | WO 2014/043054 | 3/2014 |
| WO | WO 2014/096146 | 6/2014 |
| WO | WO 2014/143815 | 9/2014 |
| WO | WO 2014/159933 | 10/2014 |
| WO | WO 2014/184293 | 11/2014 |
| WO | WO 2014/192888 | 12/2014 |
| WO | WO 2014/204958 | 12/2014 |
| WO | WO 2015/032715 | 3/2015 |
| WO | WO 2015/085019 | 6/2015 |
| WO | WO 2015/151900 | 10/2015 |
| WO | WO 2016/014365 | 1/2016 |
| WO | WO 2016/022760 | 2/2016 |
| WO | WO 2016/033507 | 3/2016 |
| WO | WO 2016/142726 | 9/2016 |
| WO | WO 2017/186402 | 11/2017 |
| WO | WO 2018/153945 | 8/2018 |
| WO | WO 2018/154033 | 8/2018 |
| WO | WO 2018/172858 | 9/2018 |

OTHER PUBLICATIONS

PCT International Preliminary Report on Patentability in International Appln.No. PCT/EP2016/079039, dated Jun. 5, 2018, 7 pages.
PCT International Preliminary Report on Patentability in International Appln.No. PCT/EP2016/079040, dated Jun. 5, 2018, 6 pages.
PCT International Preliminary Report on Patentability in International Appln.No. PCT/EP2018/054323, dated Aug. 27, 2019, 7 pages.
PCT International Preliminary Report on Patentability in International Appln.No. PCT/EP2018/054464, dated Aug. 27, 2019, 7 pages.
PCT International Search Report and Written Opinion in International Appln.No. PCT/EP2016/079038, dated Feb. 17, 2017, 10 pages.
PCT International Search Report and Written Opinion in International Appln.No. PCT/EP2016/079039, dated Feb. 21, 2017, 9 pages.
PCT International Search Report and Written Opinion in International Appln.No. PCT/EP2016/079040, dated Feb. 6, 2017, 8 pages.
PCT International Search Report and Written Opinion in International Appln.No. PCT/EP2018/054323, dated May 4, 2018, 11 pages.
PCT International Search Report and Written Opinion in International Appln.No. PCT/EP2018/054464, dated May 23, 2018, 10 pages.
U.S. Appl. No. 15/779,657, filed May 29, 2018, Hardy Kietzmann.
U.S. Appl. No. 15/779,650, filed May 29, 2018, Hardy Kietzmann.
U.S. Appl. No. 17/082,093, filed Oct. 28, 2020, Hardy Kietzmann.
U.S. Appl. No. 15/779,747, filed May 29, 2018, Hardy Kietzmann.
U.S. Appl. No. 17/063,962, filed Oct. 6, 2020, Hardy Kietzmann.
U.S. Appl. No. 16/487,006, filed Aug. 19, 2019, Hardy Keitzmann.

\* cited by examiner

PACKAGING ASSEMBLY

CROSS-REFERENCE TO RELATED APPLICATIONS

The present application is a continuation of U.S. patent application Ser. No. 16/487,013, filed on Aug. 19, 2019, which is the national stage entry of International Patent Application No. PCT/EP2018/054323, filed on Feb. 22, 2018, and claims priority to European Application No. 17305210.1, filed on Feb. 24, 2017, the disclosures of which are incorporated herein by reference.

TECHNICAL FIELD

The application relates to a packaging assembly for a medicament and, in particular, although not exclusively, to a packaging assembly configured to provide a reminder alert at a scheduled dosing time.

BACKGROUND

Patients suffering chronic disease require regular treatment with medicaments, e.g. on the basis of a predefined schedule. Particular medicaments require refrigerated storage, and are often stored refrigerated in a household refrigerator or fridge. In a home treatment environment, the patient stores the medicament in their fridge and administers a predefined dose as required. Hence, the medicament is typically provided in a secondary packaging for convenient placement and storage in the household fridge. However, the medicament must be stored together with other items that require constant refrigeration, such as foodstuffs and beverages.

Depending on the dosage form of the medicament, the secondary packaging containing the medicament may store a primary packed medicament itself, or may store one or more different kinds of drug delivery devices. For instance, the medicament may be provided in a pre-filled syringe or pen-type injector.

A medicament may have a predefined dosing schedule which requires the administration of a dose at relatively long intervals, for instance every two or four weeks, or once a month. The medicament may be provided in a secondary packaging containing several doses which may be stored in the fridge for 1 to 6 months for instance. It can be difficult for patients to keep track of each scheduled dosing time.

SUMMARY

According to an embodiment, a packaging assembly is provided according to the claims.

These and other aspects of the disclosure will be apparent from and elucidated with reference to the embodiments described hereinafter.

BRIEF DESCRIPTION OF THE FIGURES

Embodiments of the disclosure will now be described, by way of example only, with reference to the accompanying drawings, in which.

DETAILED DESCRIPTION

Figure 1:
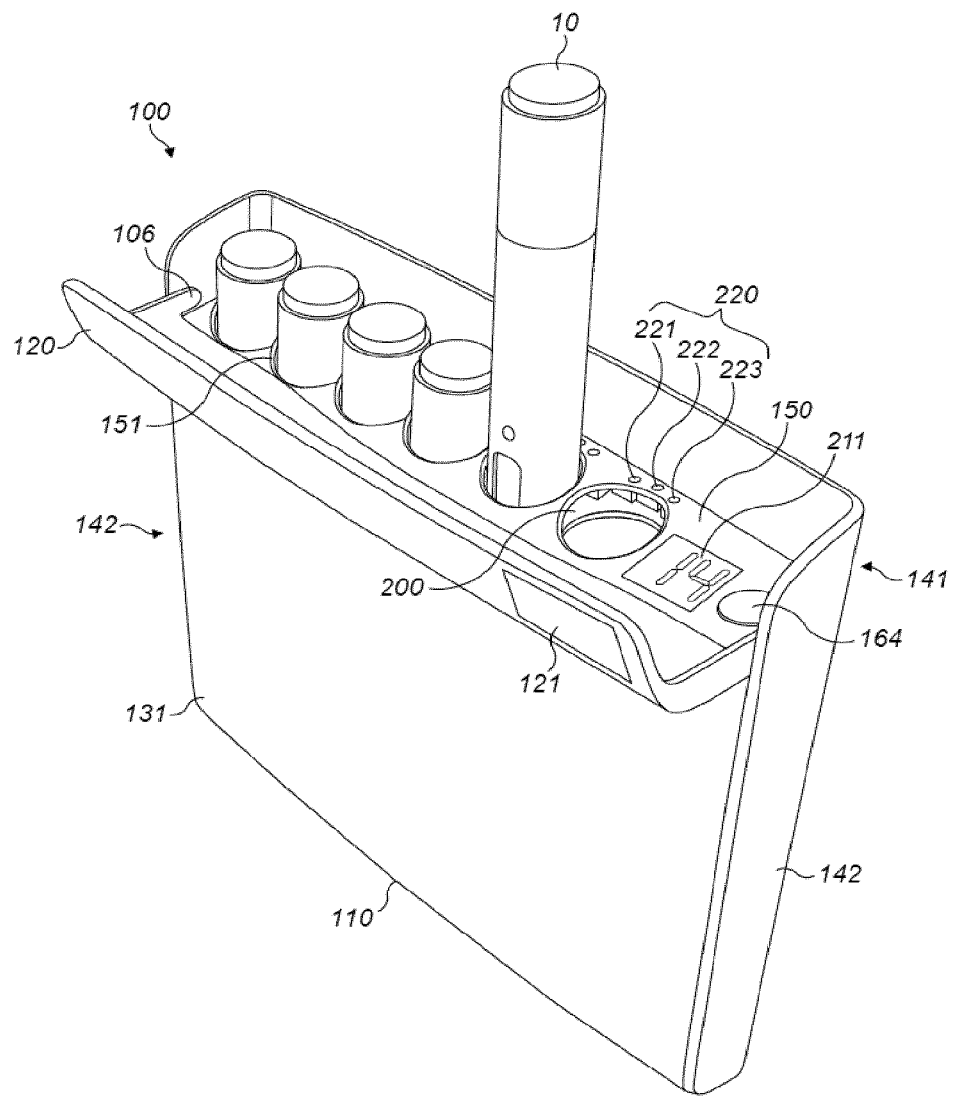
FIG. 1 is an isometric view of a packaging assembly according to a first exemplary embodiment.

Embodiments of the disclosure provide a packaging assembly configured to contain and store a plurality of injection devices for delivering a medicament. An injection device is an example of a drug delivery device and may be a pen-injector or an auto-injector. The packaging assembly is configured to detect the injection devices stored therein, and may be configured to contain a plurality of types of injection device. The packaging assembly is configured to provide an audio and/or visual reminder to a patient at a scheduled dosing time for each injection device. The packaging assembly may further include one or more user interface elements for providing the patient with a status and information relating to a status of the packaging assembly. The packaging assembly provides a predictable, easy to use operation for the patient.

The packaging assembly may be stored in a household refrigerator or fridge. The packaging assembly may include a door open sensor to determine whether or not the fridge is open. The packaging assembly may be configured to provide the reminder or a user interface output conditional on the fridge door being open. The packaging assembly provides information easily and intuitively, and allows safe storage in a fridge for convenient and discreet use by the patient.

The packaging assembly may determine whether or not the packaging assembly has been opened. The packaging assembly may deactivate the reminder upon detection of the packaging assembly being opened. The operation of the packaging assembly is predictable and intuitive for the patient.

A drug delivery device, as described herein, may be configured to inject a medicament into a patient. For example, delivery could be sub-cutaneous, intra-muscular, or intravenous. Such an injection device could be operated by a patient or care-giver, such as a nurse or physician, and can include various types of safety syringe, pen-injector, or auto-injector. The injection device can include a cartridge-based system that requires piercing a sealed ampule before use. Volumes of medicament delivered with these various injection devices can range from about 0.2 ml to about 3 ml. Yet another injection device can be represented by a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described injection devices may also be customized to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, an injection device will often include a hollow needle ranging from about 25 to about 31 Gauge in size. Common sizes are 27 and 29 Gauge.

The injection devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may be activated via an activation mechanism. Such an activation mechanism can include one or more of a button, a lever, a needle sleeve, or other activation component. Activation may be a one-step or multi-step process. That is, a user may need to activate one or more activation mechanisms to cause the automated function. For example, a user may depress a needle sleeve against their body to cause injection of a medicament. In other devices, a user may be required to depress a button and retract a needle shield to cause injection.

In addition, such activation may activate one or more mechanisms. For example, an activation sequence may activate at least two of needle insertion, medicament injection, and needle retraction. Some devices may also require a specific sequence of steps to cause the one or more automated functions to occur. Other devices may operate with sequence independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

With reference to FIG. 1, a packaging assembly 100 according to exemplary embodiments is shown. The packaging assembly 100 comprises a case 110 having a lid 120. The case 110 comprises a lower face 131, an upper face 141, and two side walls 142. The lower face 131 is curved so as to meet the upper face 141 at the rear of the device. At a front end of the case 110, an opening is formed between lower face 131, the upper face 141 and the two side walls 142.

The lid 120 of the case 110 is arranged to cover the opening of the case 110. The lid 120 is attached between the two side walls 142 of the case 110 in a hinged manner. The lid 120 can be freely moved in a hinged manner between a closed position and an open position. In the closed position, the lid 120 is arranged to cover the opening of the case 110. In the open position, the opening of the case 110 is uncovered and an interior of the case 110 can be accessed.

The lid 120 may comprise a latching mechanism to hold the lid 120 in the closed position. The latching mechanism may comprise a protruding part arranged at an edge of the lid 120. The protruding part may be configured to engage with a corresponding feature in the case 110 when the lid is in the closed position. The protruding part may be flexible or retractable to disengage from the case 110 and allow the lid 120 to move to the open position.

The case 110 is configured to hold and store a plurality of injection devices 10. A length of the case 110, measured between the rear of the case and the lid 120, is sufficient to accommodate the length of each of the injection devices 10. The length of the case may be between 160 mm and 180 mm. A depth of the case 110, measured between the top face 141 and the lower face 131, is sufficient to accommodate the width of each of the injection devices 10. The depth of the case may be between 30 mm and 40 mm. A width of the case 110, measured between the two side walls 142, is sufficient to accommodate six injection devices 10. The width of the case may be between 180 mm and 200 mm. In some examples, the case may be 188.7 mm wide, 174.7 mm high and 34 mm deep.

As shown in FIG. 1, the lower face 131 of the case 110 is shorter than the upper face 141. The lid 120 extends from a front edge of the lower face 131 to a front edge of the upper face 141. The lid 120 is curved. The curve allows the lid 120 to form the front and a portion of the bottom of the case 110 in the closed position. Other lid configurations are also contemplated.

The lower face 131, the upper face 141 and the two side walls 142 are formed from an opaque material, for example, an opaque plastic material. The lid 120 is formed from a translucent or frosted material, for example, a clear plastic material with a frosted coating or a treated surface. A portion of the lid 120 is clear and transparent to form a viewing window 121 through the lid 120.

The case 110 further comprises a panel 150 arranged within the opening. The panel 150 is visible only when the lid 120 of the case 110 is in an open position; when the lid 120 is in the closed position, the lid obscures the panel 150 from view. The panel 150 comprises a plurality of openings 151. The openings 151 are configured to hold a corresponding plurality of injection devices 10. The openings 151 in the panel 150 are circular in shape. The openings 151 may be square shaped, or rectangular shaped to accommodate other sizes of injection device 10. The width of each opening is sufficient to accommodate the width of each injection device 10. The panel 150 comprises a row of six openings, so as to hold six injection devices 10 arranged in a row along a width of the case 110.

The packaging assembly 100 may be configured to hold more than six, or fewer than six injection devices 10 in the case 110.

The lid 120 may be configured to retain the plurality of injection devices 10 in position within the case 110 when in the closed position. The lid 120 may be arranged in the closed position to prevent the injection devices 10 from falling or sliding out of the case 110. Each injection device 10 may be retained in position within the corresponding opening 151 by a friction fit with the opening 151.

A retention mechanism may retain the plurality of injection devices 10 in position within the openings 151. The retention mechanism may comprise a mechanical catch configured to engage with each injection device 10, for example, a sprung push-catch push-release mechanism. The injection device 10 is pushed into the opening 151 and pushed against a spring of the retention mechanism to engage a catch, the injection device 10 is pushed a second time to release the catch. A release button or switch may be provided for each of the openings 151, which is configured to release the catch of the retention mechanism when pressed.

A user may receive the packaging assembly 100 in an empty condition. When the user is supplied with a plurality of injection devices 10 they can be loaded into the packaging assembly 100. The lid 120 is moved into the open position and each of the injection devices 10 is inserted into a corresponding one of the openings 151. The lid 120 is moved into the closed position. The packaging assembly 100 is placed in the fridge until the first scheduled dosing time is due. The packaging assembly 100 may be placed in the fridge before or after the initial insertion of injection devices 10.

For example, a dosing time for one type of injection device 10 may be scheduled every 14 days or 28 days, according to the prescription and/or product patient leaflet of the medicament provided with the injection device 10. For some injection devices 10, a period of time between scheduled dosing times may be between 2 days and 60 days, according to the requirements of the medicament. The packaging assembly 100 may be configured to contain and store injection devices 10 of multiple types, simultaneously or at different points in time. The packaging assembly 100 may contain a plurality of injection devices 10 providing one or more different medicaments with one or more different dosing intervals.

The packaging assembly 100 is configured to provide the user with a visual and/or audio reminder when a scheduled dosing time is due. The packaging assembly 100 is further configured to determine whether or not the fridge door is open, and to provide the reminder conditional on the fridge door being open. The packaging assembly 100 is further configured to determine whether the lid 120 is in the open position or the closed position, and to deactivate the audio reminder upon detection of the lid 120 being moved to the open position.

Figure 2A:
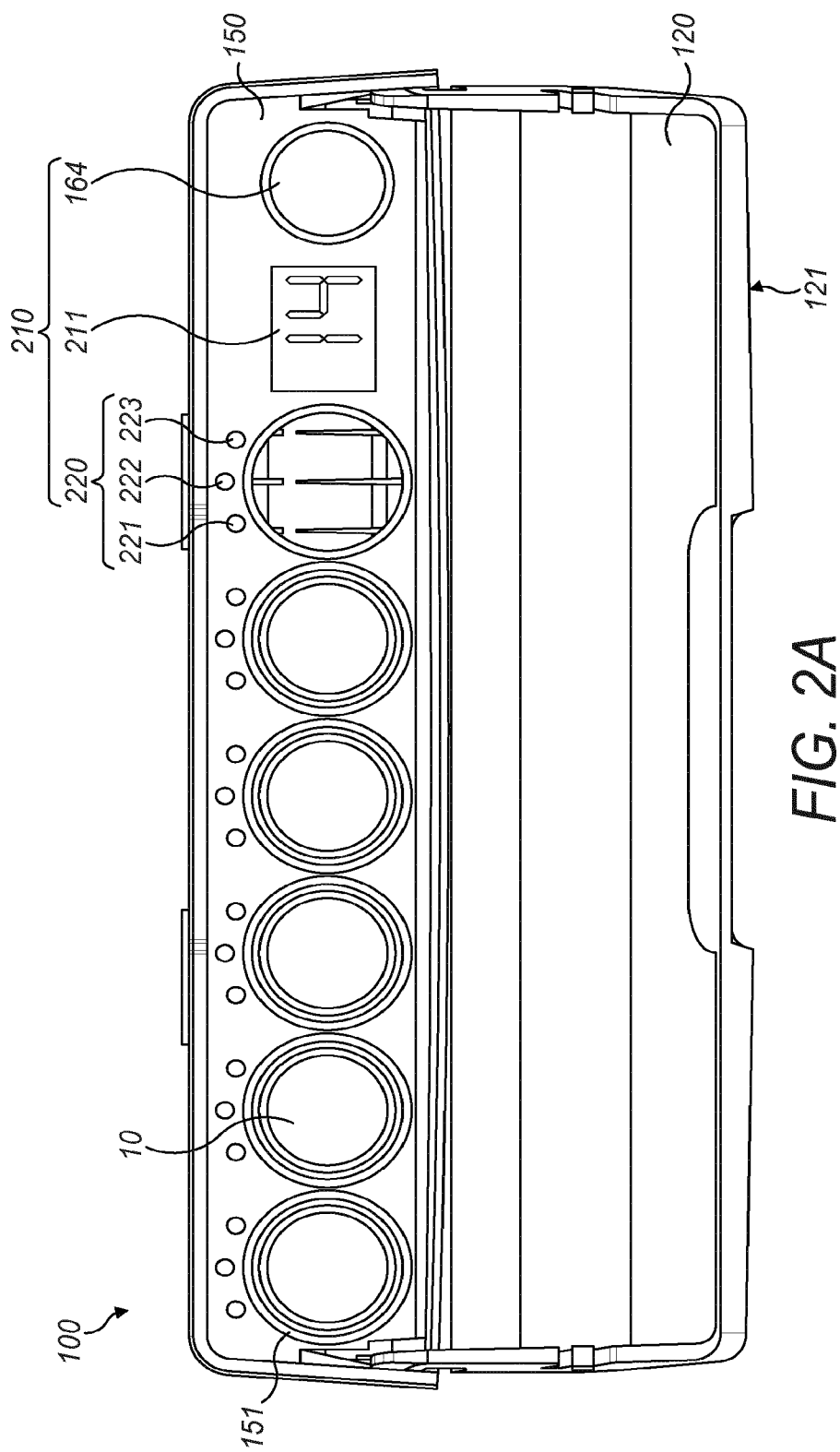
FIG. 2A is a front projection view of the packaging assembly of FIG. 1.

FIG. 2A shows the packaging assembly 100 from the front with the lid 120 in the open position. The panel 150 and openings 151 are visible. The packaging assembly 100 as shown contains a plurality of injection devices 10, each of which may be of a different device type. Different types of injection device 10 may provide different medicaments. Alternatively, different types of injection device 10 may have different dosages or concentrations of the same medicament, or different methods of delivering the medicament. Different types of injection device 10 may have different dosing intervals.

The packaging assembly 100 includes an electronics system 200. The electronics system 200 comprises multiple components that are connected together to provide a specific set of functions, described below. The components of the electronics system 200 are mounted on a printed circuit board (PCB 201), although instead they may be interconnected through some other medium.

The electronics system 200 is attached to the panel 150. Some of the electronic components of the electronics system 200 are user interface hardware components and together provide a user interface 210 for the packaging assembly 100.

The electronics system 200 comprises a display 211. The display 211 is an example of an optical transducer. The display 211 comprises two seven-segment light-emitting diode (LED) arrays. The display 211 is visible to the user through the transparent viewing window 121 in the lid 120. The electronics system 200 comprises a light-emitting diode (LED) array 220. The LED array 220 is an example of an optical transducer. The electronics system 200 comprises a reset button 164. The reset button 164 is an example of an input device. The reset button 164 is a sprung plunger button which may be depressed by the user. The electronics system 200 comprises a speaker 213 (not shown in this Figure). The speaker 213 is an example of an audio transducer.

The LED array 220 comprises an array of eighteen light-emitting diodes (LEDs). The LEDs of the LED array 220 are arranged on the panel 150, in proximity to the openings 151. The LED array 220 comprises three LEDs 221,222,223 for each of the six openings 151. Each of the three LEDs 221,222,223 can be illuminated with a different colour. For example, the LED array 220 may comprise a blue LED 221, a white LED 222 and a red LED 223 for each opening 151.

Figure 2B:
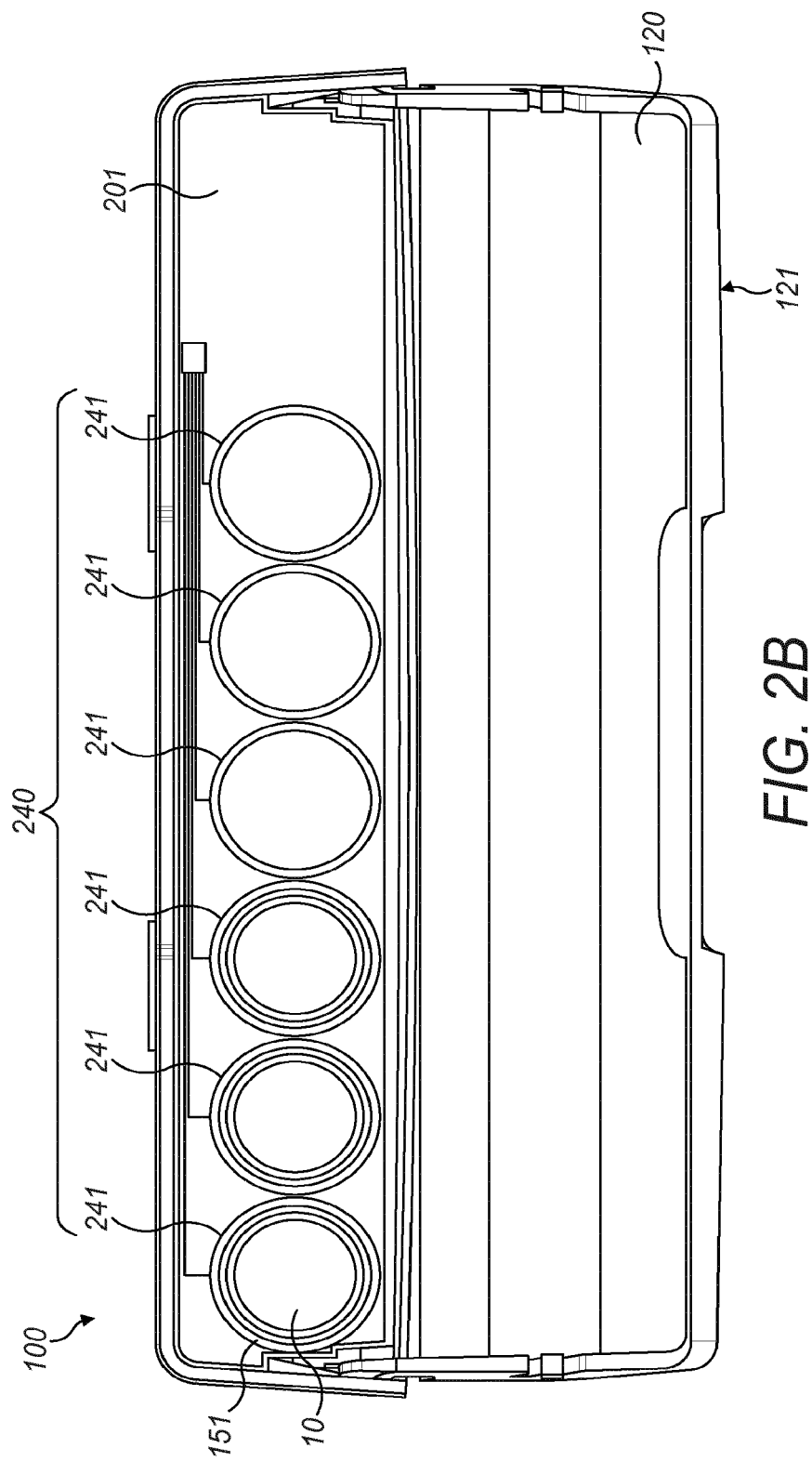
FIG. 2B is a front projection view of the packaging assembly of FIG. 1.

FIG. 2B shows an internal view of the packaging assembly 100 from the front. The rear face of the PCB 201 is illustrated.

The electronics system 200 comprises a sensor array 240. The sensor array 240 is mounted on a rear face of the PCB 201. The sensor array 240 comprises a plurality of device sensors 241. The number of device sensors 241 corresponds to the number of injection devices 10 which can be stored by the packaging assembly 100. Each device sensor 241 is mounted in proximity to one of the plurality of openings 151.

The device sensor 241 is configured to output a signal when an injection device 10 is located in the opening 151 or during insertion into opening 151. The device sensor 241 is a radio-frequency identification (RFID) reader comprising a radio-frequency antenna. Each device sensor 241 is in the form of a loop corresponding to each of the openings 151. The device sensor 241 is arranged to detect a device tag 30 arranged on the injection device 10. The device tag 30 is a passive RFID tag comprising a radio-frequency antenna. The device sensor 241 generates an electromagnetic field, which activates the device tag 30, and detects a response signal transmitted by the device tag 30. The device sensor 241 may be configured to read device information stored on the device tag 30. The processor arrangement 230 may store device information received from an injection device 10.

The sensor array 240 may include electronic components that are separate to the device sensors 241 but form part of the sensor array 240 itself. The device sensors 241 may provide signals transmitted by a device tag 30 and the electronic components perform analysis of the signal and communication to the processor arrangement 230. Alternatively, each device sensor 241 may include electronic components to perform analysis of a detected signal. Further alternatively, the analysis of incoming signals may be performed by the processor arrangement 230.

Figure 6:
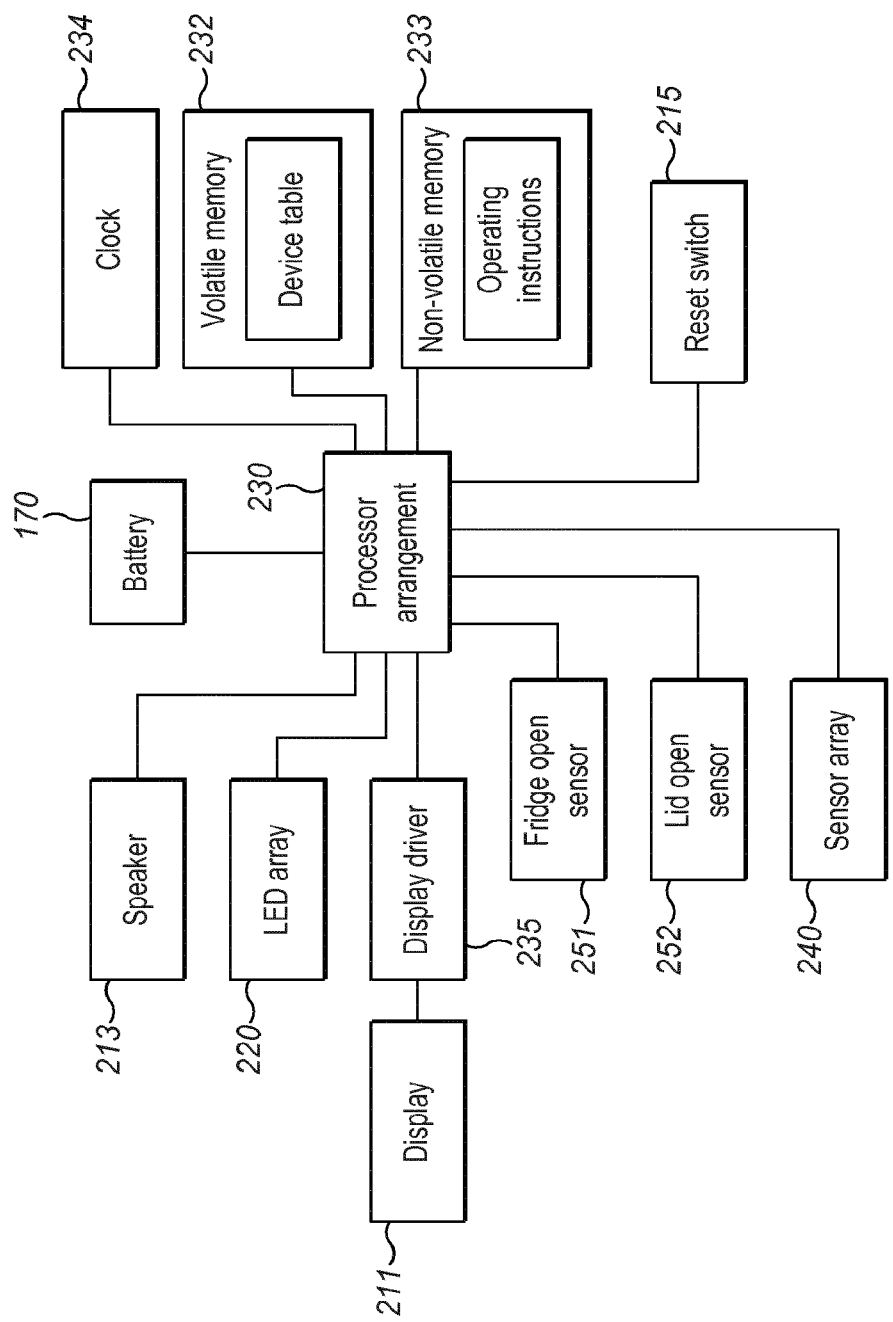
FIG. 6 is a block diagram of an electronics system of the packaging assembly, according to an exemplary embodiment.

The electronics system 200 is shown schematically in FIG. 6. The electronics system 200 comprises a processor arrangement 230. The processor arrangement 230 controls operation of the other hardware components of the electronics system 200. The processor arrangement 230 is configured to control the hardware components which form the user interface 210. The processor arrangement 230 is configured to process one or more input signals from at least one input sensor.

Figure 3:
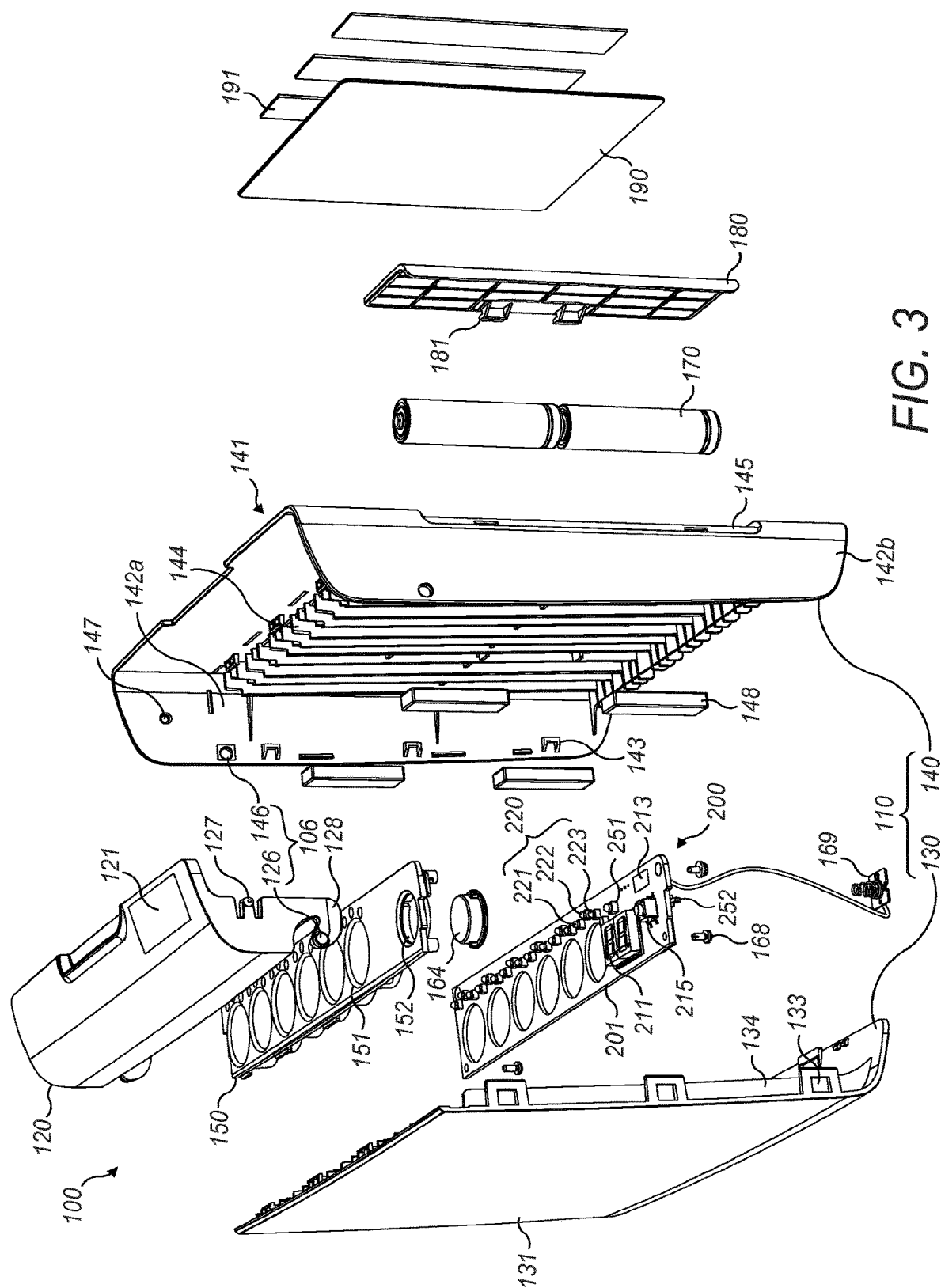
FIG. 3 is an exploded view of the packaging assembly of FIG. 1.

With reference to FIG. 3, an exploded view of the packaging assembly 100 according to the first embodiment is shown. The case 110 of the packaging assembly 100 comprises a first part 130 and a second part 140. The first part 130 of the case 110 is formed from a single piece. The first part 130 of the case 110 comprises the lower face 131 and the rear of the packaging assembly 100. Along each side edge of the lower face 131, a plurality of openings 133 are formed for engaging with the second part 140 of the case 110. Three openings 133 are formed along each edge of the first part 130. The first part 130 further comprises a plurality of dividers 134 for holding the plurality of injection devices 10 (not shown in FIG. 3) in position within the case 110.

The second part 140 comprises the upper face 141, a first side wall 142a and a second side wall 142b of the case 110. The second part 140 is formed from a single piece. The second part 140 further comprises a plurality of dividers 144 for holding and storing the plurality of injection devices 10 in position within the case 110. The dividers 144 of the second part 140 are aligned with the dividers 134 of the first part 130.

The case 110 of the packaging assembly 100 comprises a plurality of magnets 148. The magnets 148 are fixed in position on an internal side of the upper face 141. The case comprises four magnets 148 fixed in a square arrangement. The plurality of magnets 148 allows the upper face 141 of the case 110 to be releasably attached to a magnetic surface, for example, a steel surface. The magnets 148 may be neodymium magnets.

The packaging assembly 100 further comprises a mounting plate 190. The mounting plate 190 comprises a plurality of adhesive strips 191. The mounting plate 190 can be fixed to a surface using the adhesive strips 191, such as, for example, a wall or under a shelf within a fridge. The mounting plate 190 is formed from a magnetic material, for example, steel. The case 110 can be releasable attached to the surface by magnetically attaching to the beforehand fixed mounting plate 190.

The mounting plate 190 comprises three adhesive strips 191. The adhesive strips 191 are arranged in parallel across the width of the mounting plate 190 and each adhesive strip 191 extends along substantially the full length of the mounting plate. Alternatively, the mounting plate 190 may comprise only two adhesive strips 191 which are spaced apart on the mounting plate 190, or may comprise more than three adhesive strips 191 extending in parallel. Further alternatively, the mounting plate 190 may comprise four adhesive strips 191 positioned in a rectangular arrangement, for example, at each corner of the mounting plate 190. The mounting plate may comprise any number of adhesive strips 191 arranged in a regular array.

The mounting plate 190 may alternatively be placed, without adhesive, on an upper side of a shelf. The case 110 may be magnetically held beneath the shelf through a magnetic attraction to the mounting plate 190.

The packaging assembly 100 further comprises a plurality of batteries 170. The batteries 170 are arranged to provide power to the components of the electronic system 200, including the user interface 210. The second part 140 of the case 110 comprises a battery opening 145 formed in the upper face 141. The battery opening 145 is configured to receive the plurality of batteries 170. A battery cover 180 is configured to slidably engage with the battery opening 145 of the second part 140 and to cover the battery opening 145 when the packaging assembly 100 is in use. The battery cover 180 comprises a plurality of latches 181 arranged to engage with the second part 140 of the case 110.

Each of the first side wall 142a and the second side wall 142b of the case 110 comprises a plurality of engaging hooks 143. The engaging hooks 143 are arranged on an inner face of the respective side wall. Each of the side walls 142 comprises three engaging hooks 143. The engaging hooks 143 are each configured to engage with the corresponding opening 133 in the first part 130 of the case 110. Each of the side walls 142 comprises a first hinging part 146. Each of the side walls 142 comprises a first latching part 147.

The lid 120 of the case 110 comprises a second hinging part 126 configured to engage with the first hinging part 146 of the second part 140 of the case 110. The first hinging part 146 and the second hinging part 126 together form a hinge 106 for attaching the lid 120 to the second part 140 of the case 110. For example, the first hinging part 146 comprises an opening and the second hinging part 126 comprises a protrusion arranged to fit within the opening of the first hinging part 146. The second hinging part 126 is configured to rotate within the opening of the first hinging part 146.

The lid 120 of the case 110 comprises a second latching part 127 configured to engage with the first latching part 147 of the second part 140 of the case 110. The second latching part 127 is configured to releasably engage with the first latching part 147 to maintain the lid 120 in a closed position. For example, the first latching part 147 comprises an opening and the second latching part 127 comprises a protrusion configured to releasably engage with the opening of the first latching part 147.

The lid 120 is formed from a translucent plastic material. A portion of the lid 120 is clear and transparent to form a viewing window 121 through the lid 120.

The panel 150 is held in position between the first part 130 and the second part 140 of the case 110. The panel 150 comprises the plurality of openings 151. The openings 151 are configured to hold the corresponding plurality of injection devices 10. The panel 150 further comprises one or more openings 152 for the hardware components of the user interface 210. The packaging assembly 100 comprises the electronics system 200. The electronics system 200 includes the hardware components of the user interface 210, namely the display 211, the LED array 220, the speaker 213 and the reset button 164. The display 211 of the user interface 210 is visible through the transparent viewing window 121 of the lid 120.

A plurality of screws 168 are arranged to attach a support of the electronics system 200, for instance a PCB 201, to a rear face of the panel 150. The sensor array 240 is mounted on the rear face of the PCB 201. Alternatively, the sensor array 240 may be arranged on the front face of the PCB 201. Further alternatively, the sensor array 240 may be arranged on the rear face of the panel 150. The electronics system 200 is coupled with a battery contact 169. The battery contact 169 is mounted with the plurality of batteries 170 to supply power to the electronics system 200.

The electronics system 200 comprises a reset switch 215. The reset button 164 is a sprung plunger button arranged to be pushed by the user. The reset switch 215 is a mechanical switch mounted on the electronics system 200. The reset switch 215 is positioned below the reset button 164. The reset switch 215 is arranged to be actuated by the reset button 164. The reset button 164 may be coupled to the reset switch 215.

The electronics system 200 comprises a light sensor 251. The light sensor 251 is mounted on the PCB 201 of the electronics system 200. The light sensor 251 comprises a phototransistor configured to pass a current according to the amount or intensity of light which is incident on the light sensor 251. The light sensor 251 is an example of a fridge open sensor.

The light sensor 251 may be of the type where the inherent device characteristics are such that an intensity of light exceeding a threshold results in a signal of one type (e.g. high) and an intensity of light below the threshold results in a signal of an opposite type (e.g. low). Alternatively, comparison of the intensity to a threshold may be performed by electronic components that are separate to the device of the light sensor 251 but form part of the light sensor itself. Here, the light sensitive device provides a signal with a level that varies according to the detected light intensity and the electronic components perform analysis of the signal compared to a threshold.

Further alternatively, the comparison may be performed in the digital domain by the processor arrangement 230. Here, the light sensor provides a signal with a level that varies according to the detected light intensity, this is converted by an analogue to digital converter (if not already a digital signal) and the processor arrangement compares the signal to a threshold. Unless the threshold is inherent in the device, the threshold may be preset (that is, predetermined and set at the design or manufacture stage) or it may be dynamically adjustable having regard to operating conditions.

The arrangement may be configured to filter out short duration bursts of light exceeding the threshold, which filtering may occur through the use of slow response components, so as to reduce the occurrence of false triggering. As will be appreciated, if there is false triggering from short duration periods of light intensity exceeding the threshold, the result is short duration activation of user interface components.

The electronics system 200 comprises a hinge switch 252. The hinge switch 252 may be an electro-mechanical switch such as a microswitch or other miniature snap action switch. The hinge switch 252 is an example of a lid open sensor.

The hinge switch 252 is arranged to engage with the lid 120 of the case 110 when the lid 120 is in a closed position. An actuating part 128 of the lid 120 is shaped so as to press the hinge switch 252 when the lid 120 is in a closed position. The hinge switch 252 is mounted at an edge of the PCB 201 of the electronics system 200. The actuating part 128 of the lid 120 is arranged to pass the edge of the PCB 201 of the electronics system 200 when the lid 120 is in a closed position.

The electronics system 200 further comprises the processor arrangement 230 (not shown in this Figure). The processor arrangement 230 is configured to process the input signals from the one or more sensors and the switches on the electronics system 200. The processor arrangement 230 is configured to control the outputs of the user interface elements on the electronics system 200.

Figure 4A:
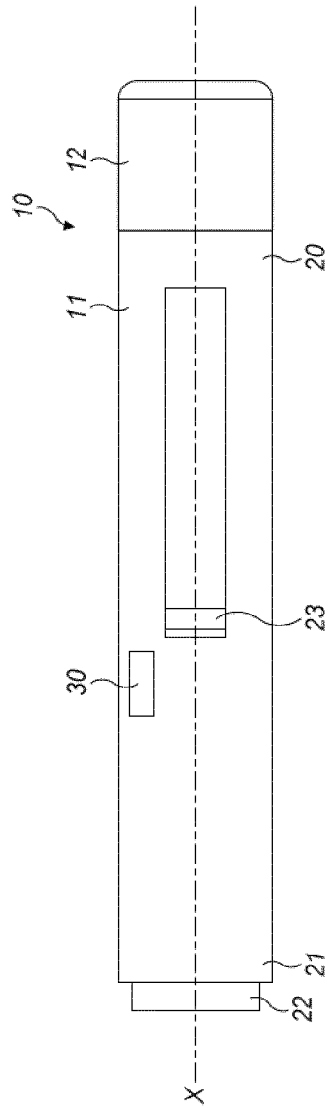
FIGS. 4A and 4B are side-on views of an auto-injection device for use with the packaging assembly, according to an exemplary embodiment.
Figure 4B:
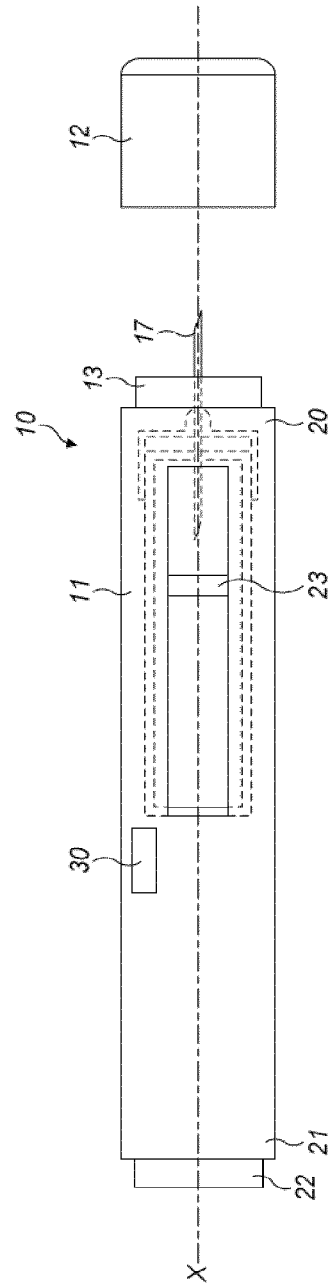

With respect to FIGS. 4A and 4B, an exemplary injection device 10 is shown. Injection device 10, as described above, is configured to inject a medicament into a user's body. Injection device 10 includes a housing 11 which typically contains a reservoir containing the medicament to be injected (e.g., a syringe) and the components required to facilitate one or more steps of the delivery process. Injection device 10 can also include a cap assembly 12 that can be detachably mounted to the housing 11. Typically a user must remove cap 12 from housing 11 before injection device 10 can be operated.

As shown, housing 11 is substantially cylindrical and has a substantially constant diameter along the longitudinal axis X. The housing 11 has a proximal region 20 and a distal region 21. The term "proximal" refers to a location that is relatively closer to a site of injection, and the term "distal" refers to a location that is relatively further away from the injection site.

Injection device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a distal direction can permit a needle 17 to extend from proximal region 20 of housing 11.

Insertion of needle 17 can occur via several mechanisms. For example, needle 17 may be fixedly located relative to housing 11 and initially be located within an extended needle sleeve 13. distal movement of sleeve 13 by placing a proximal end of sleeve 13 against a user's body and moving housing 11 in a proximal direction will uncover the proximal end of needle 17. Such relative movement allows the proximal end of needle 17 to extend into the user's body. Such insertion is termed "manual" insertion as needle 17 is manually inserted via the user's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 4A and 4B, button 22 is located at a distal end of housing 11. However, in other embodiments, button 22 could be located on a side of housing 11.

Other manual or automated features can include drug injection or needle retraction, or both. Injection is the process by which a bung or piston 23 is moved from a distal location within a syringe (not shown) to a more proximal location within the syringe to force a medicament from the syringe through needle 17. In some embodiments, a drive spring (not shown) is under compression before device 10 is activated. A distal end the drive spring can be fixed within distal region 21 of housing 11, and a proximal end of the drive spring can be configured to apply a compressive force to a distal surface of piston 23. Following activation, at least part of the energy stored in the drive spring can be applied to the distal surface of piston 23. This compressive force can act on piston 23 to move it in a proximal direction. Such proximal movement acts to compress the liquid medicament within the syringe, forcing it out of needle 17.

Following injection, needle 17 can be retracted within sleeve 13 or housing 11. Retraction can occur when sleeve 13 moves proximally as a user removes device 10 from a user's body. This can occur as needle 17 remains fixedly located relative to housing 11. Once a proximal end of sleeve 13 has moved past a proximal end of needle 17, and needle 17 is covered, sleeve 13 can be locked. Such locking can include locking any distal movement of sleeve 13 relative to housing 11.

Another form of needle retraction can occur if needle 17 is moved relative to housing 11. Such movement can occur if the syringe within housing 11 is moved in a distal direction relative to housing 11. This distal movement can be achieved by using a retraction spring (not shown), located in proximal region 20. A compressed retraction spring, when activated, can supply sufficient force to the syringe to move it in a distal direction. Following sufficient retraction, any relative movement between needle 17 and housing 11 can be locked with a locking mechanism. In addition, button 22 or other components of device 10 can be locked as required.

Injection device 10 comprises a device tag 30, for example, a passive RFID tag. The device tag 30 may internally or externally mounted on the housing 11. The device tag 30 is configured to activate when placed in an electromagnetic field, and to output a response signal when activated.

The device tag 30 is arranged at a midpoint of the housing 11, between proximal region 20 and distal region 21. The device tag 30 is arranged to align with the device sensor 241 when the injection device 10 is moved through the opening 151 of the packaging assembly 100. In this way, the device tags 30 of injection devices 10 stored in the packaging assembly 100 are separated from the sensor array 240, improving the clarity of detection. Furthermore, the speed of the injection device 10 is generally greatest as the midpoint of the injection device 10 is moving through the opening 151. The device tag 30 is therefore activated for a shorter period of time, and the power consumption of the device sensor 241 can be minimised.

The response signal of the device tag 30 may include information related to the injection device 10. Information may be stored on the device tag 30 and transmitted as part of the response signal when the device tag 30 is activated. The device tag 30 may store one or more of a device ID, device type, expiry date, dosing time period and warm-up time period of the injection device 10.

The packaging assembly 100 may contain or store a plurality of different types of injection device 10 with different information stored on each device tag 30. Each injection device 10 may have a different expiry date, dosing time period and/or warm-up time period stored in the device tag 30.

Figure 5:
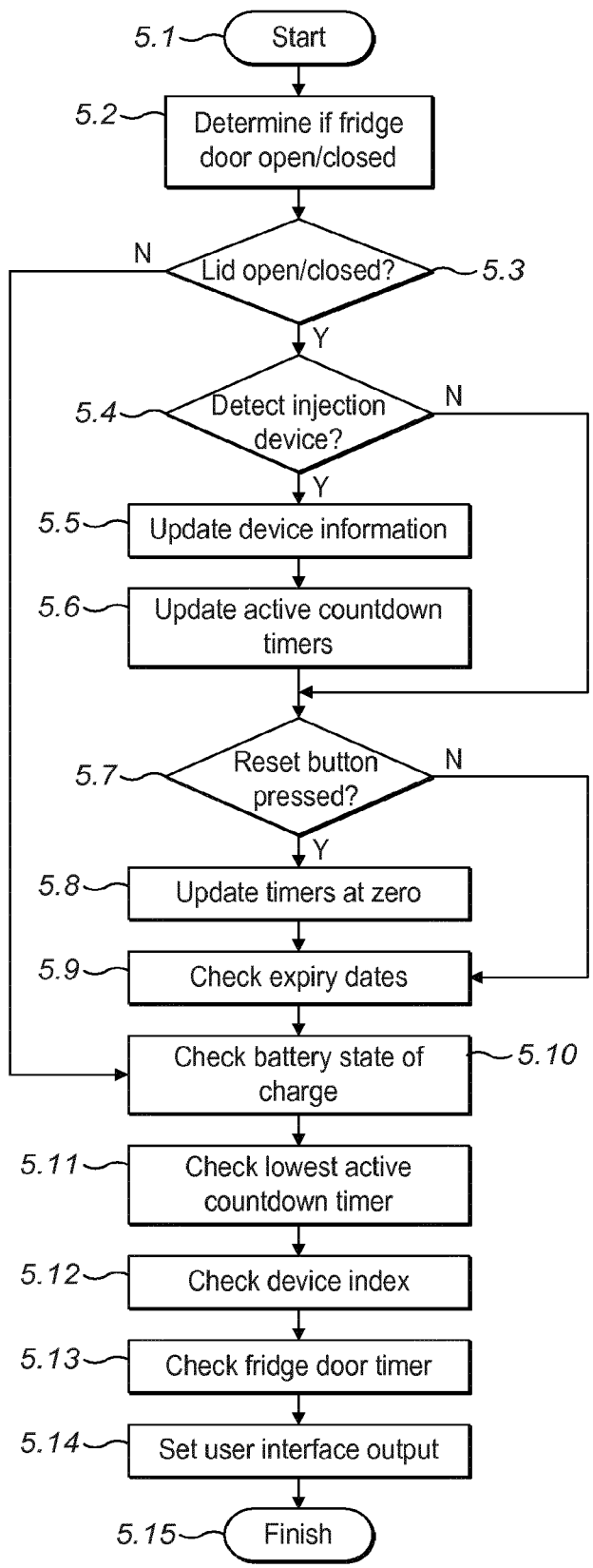
FIG. 5 is a flowchart illustrating a first exemplary operation of the packaging assembly, according to an exemplary embodiment.

A first exemplary operation of the packaging assembly 100 will now be described with reference to the flow chart of FIG. 5. In the following, actions said to be made by the packaging assembly 100 typically are made by the electronics system 200 and, in particular, by the processor arrangement 230 operating according to instructions to control the components of the electronics system 200. The flow chart of FIG. 5 is schematic.

The Operation Starts at Step 5.1.

At step 5.2, the processor arrangement 230 determines whether a fridge door of a fridge in which the packaging assembly 100 is stored is open or closed. If the fridge door is partially open, then the processor arrangement 230 determines the fridge door to be open. That is, the fridge door is determined to be open if it is not closed. If the fridge door is determined to be open, the operation proceeds to step 5.3. Otherwise, it stays at step 5.2 until the fridge door is determined to be open. The user interface 210 can be controlled by the processor arrangement 230 according to whether the fridge door is detected to be open or closed.

At step 5.3, the processor arrangement 230 determines whether the lid 120 of the packaging assembly 100 is in the open position or the closed position. The user interface 210 can be controlled by the processor arrangement 230 according to whether or not the lid 120 is open. If the lid 120 is open, the processor arrangement 230 proceeds to step 5.4. Otherwise, the processor arrangement 230 proceeds to step 5.10.

At step 5.4, the processor arrangement 230 determines whether an injection device 10 is detected by the sensor array 240. The sensor array 240 may detect an injection device 10 as the injection device 10 is moved into or out of an opening 151. If an injection device 10 is detected by the sensor array 240, the processor arrangement 230 proceeds to step 5.5. Otherwise, the processor arrangement 230 proceeds to step 5.7.

At step 5.5, the processor arrangement 230 receives device information from the detected injection device 10, and updates device information which is stored by the processor arrangement 230. The processor arrangement 230 can increase or decrease a count of the number of injection devices 10 stored in the packaging assembly 100, according to the insertion or removal of an injection device 10. Where a new injection device 10 is detected as it is inserted into an opening 151, the processor arrangement 230 can increase the count of the number of injection devices 10. Where a stored injection device 10 is detected as it is removed from an opening 151, the processor arrangement 230 can decrease the count of the number of injection devices 10. The processor arrangement updates a device index for injection devices 10 of the same type. The device index indicates the number of injection devices 10 of the same type.

The user interface 210 can be controlled by the processor arrangement 230 according to whether an injection device 10 is stored in the packaging assembly 100, and according to device information received from the injection device 10. At step 5.6, the processor arrangement 230 updates one or more active countdown timers based on the device information received from the one or more injection devices 10 and stored information about injection devices 10 stored in the packaging assembly 100. The processor arrangement 230 then proceeds to step 5.7.

At step 5.7, the processor arrangement 230 checks whether or not the reset button 164 is pressed, that is to say whether it is currently being operated by a user. If the reset button 164 is pressed, the processor arrangement 230 proceeds to step 5.8. At step 5.8, the processor arrangement 230 resets the completed countdown timer. The processor arrangement 230 resets the active countdown timers which have reached zero.

If the reset button 164 is not determined to be pressed at step 5.7, the processor arrangement 230 proceeds to step 5.9. At step 5.9, the processor arrangement 230 checks the expiry date of one or more injection devices 10 stored in the packaging assembly 100. The user interface 210 can be controlled according to the expiry date of the one or more injection devices 10.

At step 5.10, the processor arrangement 230 checks the state of charge of one or more batteries 170 included in the packaging assembly 100. The user interface 210 can be controlled by the processor arrangement 230 according to the state of change of the battery 170.

At step 5.11, the processor arrangement checks the lowest active countdown timer. The processor arrangement 230 can determine the time remaining (e.g. the number of days remaining) until the next scheduled dosing time. The user interface 210 can be controlled by the processor arrangement 230 according to whether or not the reset button 164 is pressed, and/or according to the state of the lowest active countdown timer of the processor arrangement 230.

At step 5.12, the processor arrangement 230 checks the device index of one or more injection devices 10 stored in the packaging assembly 100. The user interface 210 can be controlled according to the device index of the one or more injection devices 10. The processor arrangement 230 can remove an active countdown timer for a device type of injection device 10 based on the device index of the respective device type.

At step 5.13, the processor arrangement 230 checks a door open timer. The processor arrangement 230 monitors the amount of time that the door of the fridge has been open using the door open timer. The user interface 210 can be controlled by the processor arrangement 230 according to the door open timer of the processor arrangement 230.

At step 5.14, the processor arrangement 230 controls the hardware components of the electronics system 200 which form the user interface 210. The user interface 210 is controlled based on the determinations made at any of steps 5.2, 5.3, 5.4, 5.7, 5.9, 5.10, 5.11, 5.12 and 5.13.

The packaging assembly 100 is configured to output a reminder alert if the next scheduled dosing time is due. The packaging assembly 100 is configured to output the reminder alert conditional on the door of the fridge being open. The packaging assembly 100 is configured to deactivate the audio reminder alert upon detection of the lid 120 being moved from the closed position to the open position. The packaging assembly 100 is configured to enter a partial sleep state when the amount of time measured by the door timer is over a defined threshold time.

The packaging assembly 100 is configured to output an indication if the expiry date of one or more injection devices 10 stored in the packaging assembly 100 is passed. The packaging assembly 100 is configured to output an indication if the state of charge of one or more batteries 170 included in the packaging assembly 100 is low.

The Operation Finishes at Step 5.15.

With respect to FIG. 6, a schematic representation of the electronics system 200 of the packaging assembly 100 according to the first embodiment is shown. The electronics system 200 comprises the processor arrangement 230. The processor arrangement 230 and other hardware components may be connected via a system bus (not shown). Each hardware component may be connected to the system bus either directly or via an interface. One or more batteries 170 are arranged to provide power to the electronics system 200.

The processor arrangement 230 controls operation of the other hardware components of the electronics system 200. The processor arrangement 230 may be an integrated circuit of any kind. The processor arrangement 230 may for instance be a general purpose processor. It may be a single core device or a multiple core device. The processor arrangement 230 may be a central processing unit (CPU) or a general processing unit (GPU). Alternatively, it may be a more specialist unit, for instance a RISC processor or programmable hardware with embedded firmware. Multiple processors may be included. The processor arrangement 230 may be termed processing means.

The processor arrangement 230 has an internal processing clock speed of about 4 MHz. The processor arrangement 230 also has a stand-by clock speed of 2 Hz to reduce energy consumption. The internal processing clock speed and stand-by clock speed are selected to provide a balance between power usage and usability. A greater clock speed provides improved usability by reducing the time required for the processor arrangement 230 to respond to an input. However, a greater clock speed will increase the power usage of the processor arrangement 230. The stand by clock speed may be selected between 0.5 and 100 Hz.

The electronics system 200 comprises a working or volatile memory 232. The processor arrangement 230 may access the volatile memory 232 to process data and may control the storage of data in memory. The volatile memory 232 may be a RAM of any type, for example Static RAM (SRAM), Dynamic RAM (DRAM), or it may be Flash memory. Multiple volatile memories may be included, but are omitted from the Figure.

The electronics system 200 comprises a non-volatile memory 233. The non-volatile memory 233 stores a set of operation instructions for controlling the normal operation of the processor arrangement 230. The non-volatile memory 233 may be a memory of any kind such as a Read Only Memory (ROM), a Flash memory or a magnetic drive memory. Other non-volatile memories may be included, but are omitted from the Figure.

The processor arrangement 230 operates under the control of the operating instructions. The operating instructions may comprise code (i.e. drivers) relating to the hardware components of the electronics system 200, as well as code relating to the basic operation of the packaging assembly 100. The operating instructions may also cause activation of one or more software modules stored in the non-volatile memory 233. Generally speaking, the processor arrangement 230 executes one or more instructions of the operating instructions, which are stored permanently or semi-permanently in the non-volatile memory 233, using the volatile memory 232 temporarily to store data generated during execution of the operating instructions.

The processor arrangement 230, the volatile memory 232 and the non-volatile memory 233 may be provided as separate integrated circuit chips connected by an off-chip bus, or they may be provided on a single integrated circuit chip. The processor arrangement 230, the volatile memory 232 and the non-volatile memory 233 may be provided as a microcontroller.

The electronics system 200 comprises a clock 234. The clock 234 may be a clock crystal, for example, a quartz crystal oscillator. The clock 234 may be a separate component to the processor arrangement 230 which is configured to provide a clock signal to the processor arrangement 230. The processor arrangement 230 may be configured to provide a real time clock based on the signal from the clock 234. Alternatively, the clock 234 may be a clock crystal which is provide on a single integrated circuit chip with the processor arrangement 230.

The processor arrangement 230 is configured to perform at least one countdown operation. The processor arrangement 230 may perform a different countdown operation for each different type of injection device 10 stored in the packaging assembly 100. The processor arrangement 230 monitors the one or more countdown operations to determine the number of days remaining until the next scheduled dosing time. Countdown operations are set and activated in response to the insertion of an injection device 10 into one of the openings 151, detected by the sensor array 240. The processor arrangement 230 records the number of days for each countdown timer to the volatile memory 232 and every 24 hours reduces the recorded number of days by one.

The predetermined time period for each countdown to the next scheduled dosing time may be different for each different type of device. For example, if a time period until the next scheduled dosing time is due is 14 days for a certain type of device, the countdown timer for that type of device is started from 14 days. If a time period until the next scheduled dosing time is due is 28 days for another type of device, the countdown timer for that type of device is started from 28 days.

Every 24 hours, the number of days recorded to the volatile memory 232 is reduced by one. The processor arrangement 230 monitors the lowest active countdown to determine the number of days remaining until the next scheduled dosing time. When 1 day remains until the next scheduled dosing time, the processor arrangement 230 may control the electronics system 200 to generate an output to indicate that the next scheduled dosing time is near. On the day of the scheduled dosing time, the processor arrangement 230 may control the electronics system 200 to generate an output to indicate that the next scheduled dosing time is due. The hardware components of the electronics system 200 which form the user interface 210 may be controlled to indicate that the next scheduled dosing time is due. The user interface 210 may by controlled to indicate that the next scheduled dosing time is due for a certain device type, or for the injection device 10 stored in a certain opening 151.

On one day, for instance the first or last day, the reduction of the number of days may be provided in less than 24 hours. For instance, it may be achieved in 20 hours or 22 hours. This can help to prevent creep of the alert time to later and later in the day after multiple resets of the countdown timer. Alternatively, when the remaining number of days recorded in the volatile memory is equal to one, the processor arrangement 230 may be configured to reduce the time remaining until the next scheduled dosing time is due. For example, the processor arrangement 230 may be configured to wait only 23 hours before reducing the number of days to zero. In this way, the time of day at which the scheduled dosing time becomes due is one hour earlier than the time at which the reset button 164 was pressed.

The processor arrangement 230 may be configured to perform one or more timing operations. For example, the processor arrangement 230 may operate a door timer to monitor the amount of time that the door of the fridge has been open. The processor arrangement 230 may operate a reset timer to monitor the amount of time that the reset button 164 has been pressed. The processor arrangement 230 may start a timing operation from zero and monitor an increasing amount of time. Alternatively, the processor arrangement 230 may start a timing operation from a predetermined time and count down until the timer expires.

The processor arrangement 230 may be configured to provide a current date and time based on the signal from the clock 234. The processor arrangement 230 may monitor the expiry date for each injection device 10 stored in the packaging assembly 100. The processor arrangement 230 may determine that an injection device 10 has expired when the expiry date is in the past. The processor arrangement 230 may control the electronics system 200 to generate an output to indicate that an injection device 10 has expired.

The processor arrangement 230 may be configured to check the state of charge of one or more batteries 170 included in the packaging assembly 100. The state of charge is determined to be low if it is below a threshold (which may be built into the design of the packaging arrangement). The state of charge may be determined by measurement of the voltage provided by the battery 170, by monitoring energy use from a full state of charge, or a combination of these two techniques.

The electronics system 200 comprises a fridge open sensor 251. The fridge open sensor 251 may be a light sensor, for example a phototransistor, mounted on the electronics system 200. The fridge open sensor 251 is configured to provide a signal to the processor arrangement 230 when light is incident on the phototransistor. For example, when the packaging assembly 100 is stored within a fridge, the fridge open sensor 251 may provide an indication that a door of the fridge is open by providing a signal when ambient light from outside the fridge, or light from an internal fridge light, is incident on the phototransistor. When the fridge door is closed, no light is incident on the phototransistor and the fridge open sensor 251 provides no signal or a small signal.

The fridge open sensor 251 may comprise a phototransistor configured to pass a current according to the amount or intensity of light which is incident on the phototransistor. The fridge open sensor 251 may be configured to provide a signal of one type (e.g. high) when an intensity of incident light exceeds a threshold, and a signal of an opposite type (e.g. low) when an intensity of incident light is below the threshold.

Alternatively, the fridge open sensor 251 provides a current signal to the processor arrangement 230 according to the intensity of light which is incident on the phototransistor. The received signal may be compared to a threshold by the processor arrangement 230. The threshold may be a preset threshold stored in the non-volatile memory 233, or it may be dynamically adjustable having regard to operating conditions.

The processor arrangement 230 is configured to determine whether a door of a fridge in which the packaging assembly 100 is stored is open or closed, based on a signal received from the fridge open sensor 251.

The processor arrangement 230 is configured to start a door timer when the fridge door is opened. The processor arrangement 230 starts the door open timer in response to a signal from the light sensor 251 to indicate that the fridge door is open. The signal from the light sensor 251 may be used to trigger an interrupt port input to the processor arrangement 230. After the timer has been started, the device can be said to be in a door open state. When the fridge door is closed, the device can be said to be in a door closed state.

The processor arrangement 230 may be configured to enter a partial sleep state when the time period measured by the door timer is over a threshold time. For example, the processor arrangement 230 may enter a partial sleep state when the fridge door has been open for 5 minutes. The door open timer may be configured to expire after a predetermined time, for instance in the range of 1 minute to 10 minutes. The processor arrangement 230 may control the electronics system 200 not to generate an output in the partial sleep state. In the door closed state and in the partial sleep state the processor arrangement 230 changes to the stand-by clock speed to reduce power usage.

The device transitions from the door open state to the partial sleep state when the door timer passes the 5 minutes mark. The door timer may be started at 5 minutes when the door is detected to be opened and count down such that the timer expires if the door is not closed within 5 minutes.

The electronics system 200 comprises a lid open sensor. The lid open sensor 252 is configured to provide a signal to the processor arrangement 230 when the lid 120 of the case 110 in a closed position.

The lid open sensor 252 may be a hinge switch, for example an electro-mechanical switch such as a microswitch or other miniature snap action switch. The lid open sensor 252 may be arranged to mechanically engage with the lid 120 when the lid 120 is in a closed position. An actuating part 128 of the lid 120 may be shaped to engage with the lid open sensor 252 when the lid 120 is in a closed position. The lid open sensor 252 may be a normally open switch having an open state and a closed state. The switch may be operated to move from the open state to the closed state when pressed. The switch may be configured to pass a current in a closed state only.

The lid open sensor 252 may be configured to provide a signal to the processor arrangement 230 when the switch is pressed into the closed state by the lid 120. The processor arrangement 230 may be configured to set a variable to indicate whether or not the lid 120 has been opened. The processor arrangement 230 may store a lid flag. The processor arrangement 230 may set the lid flag to have a value of 1 when the lid open sensor 252 indicates that the lid 120 has been opened.

The electronics system 200 comprises a sensor array 240. The sensor array 240 is arranged to detect one or more injection devices 10 inserted into or removed from the packaging assembly 100. The sensor array 240 is configured to detect whether or not an injection device 10 is moved through each of the openings 151. The sensor array 240 provides a signal to the processor arrangement 230 to indicate the presence of an injection device 10 in each of the openings 151. The processor arrangement 230 stores a device table in the volatile memory 232 which records whether or not an injection device 10 is stored in each of the openings 151.

The sensor array 240 comprises a plurality of device sensors 241. The number of device sensors 241 in the sensor array 240 corresponds to the number of injection devices 10 which can be stored in the packaging assembly 100. The sensor array 240 comprises one device sensor 241 for each of the openings 151.

A device sensor 241 comprises a radio-frequency (RF) antenna mounted in proximity to the corresponding opening 151. The processor arrangement 230 operates the device sensor 241 to transmit an RF electromagnetic signal through the antenna. When an injection device 10 is located at the opening 151, the electromagnetic signal activates a device tag 30 on the injection device 10. The device tag 30 comprises an RF antenna and a low power circuit. The device tag 30 is powered through induction by the RF signal broadcast by the device sensor 241.

The device tag 30 is arranged at a midpoint on the length of the injection device 10. The device tag 30 is activated when the midpoint of the injection device 10 passes through the opening 151. When activated, the device tag 30 transmits a response signal through the RF antenna. The device sensor 241 detects the response signal transmitted by the device tag 30 and provides a signal to the processor arrangement 230. The processor arrangement 230 determines whether the injection device 10 is being inserted into the opening 151 or removed from the opening 151, according to the information in the device table. The processor arrangement 230 updates the device table according to whether the injection device 10 is being inserted into the opening 151 or removed from the opening 151.

The device sensor 241 may receive device information from the device tag 30. The device tag 30 may comprise a non-volatile storage with stored device information. The device tag 30 may be configured to transmit the device information with the response signal when activated by the device sensor 241. The device tag 30 may store one or more of a device ID, a device type, an expiry date, a dosing time period and a warm-up time period for the injection device 10. The device sensor 241 may receive the device information transmitted with the response signal from the device tag 30. The device sensor 241 sends the received device information to the processor arrangement 230.

The sensor array 240 is operated by the processor arrangement 230 to scan for one or more injection devices 10 when the lid 120 is open and the packaging assembly 100 is in usual working mode. The processor arrangement 230 updates the device table based on device information received from the sensor array 240.

The processor arrangement 230 receives device information for each injection device 10 inserted into or removed from the packaging assembly 100. The processor arrangement 230 is configured to store received device information in the volatile memory 232. The received device information is stored in the volatile memory 232 in a device table. An exemplary device table is shown below in Table 1.

TABLE 1 device information stored in volatile memory

| Device | Device ID | Device Type | Device Index | Dosing Period | Expiry Date | Expired |
|---|---|---|---|---|---|---|
| 1 | #213451 | #0001 | 01 | 28 days | DDMMYYYY | |
| 2 | #234534 | #0001 | 02 | 28 days | DDMMYYYY | |
| 3 | #467655 | #0002 | 01 | 14 days | DDMMYYYY | |
| 4 | #567567 | #0002 | 02 | 14 days | DDMMYYYY | Y |
| 5 | #643544 | #0002 | 03 | 14 days | DDMMYYYY | Y |
| 6 | NULL | | | | | |

The processor arrangement 230 stores the device ID, device type, dosing time period and expiry date received from each device tag 30 in the device table. The device table includes an entry for each injection device 10 stored in the packaging assembly 100. The processor arrangement 230 records a NULL entry for each empty position in the packaging assembly 100.

The device ID represents a unique identifier for the injection device 10. Each injection device 10 has a unique device ID recorded on the device tag 30. The device type is related to the specific treatment provided by the injection device 10. The device type may be defined by any feature which differentiates injection devices 10 for different treatments. For example, the device type may be defined by one or more of the medicament contained in each injection device 10, the volume or concentration of the medicament and the method of administration. The device type may be represented by one field in the device table or, alternatively, may be represented by two or more distinct fields.

The processor arrangement 230 records a device index for each injection device 10. The device index relates to the number of injection devices 10 of each type stored in the packaging assembly 100. Injection devices 10 of the same type are assigned distinct numerical device indices in sequence by the processor arrangement 230. The highest device index for a certain device type in the device table indicates the number of injection devices 10 of the certain type stored in the packaging assembly 100. The processor arrangement 230 may separately record the device index for each device type. The device index for a device type is "0" when no injection device 10 of that type is stored in the packaging assembly 100.

The device ID may be validated by the processor arrangement 230. The processor arrangement 230 may operate the user interface 210 to output a visual indication if a device ID is not recognised by the processor arrangement 230.

If a new device type of injection device 10 is detected by the sensor array 240, the processor arrangement 230 initiates a new countdown timer based on the dosing time period for that device type. If a countdown timer is not active for a device type of injection device 10, for example, if the device type is newly introduced to the packaging assembly 100, or if a previous countdown timer for that device type has been removed, a new countdown timer is initiated based on the dosing time period for the device type.

If an active countdown timer is determined to be redundant, the processor arrangement 10 removes the redundant countdown timer. For example, if an injection device 10 is removed and the treatment is no longer going to be continued, the processor arrangement 10 is configured to remove the redundant countdown timer. When the active countdown time reaches zero, the processor arrangement 10 is configured to check the device index and determine whether an injection device 10 of the correct type is stored in the packaging assembly 100. If no injection device 10 of the correct time is stored in the packaging assembly 100, the countdown timer is removed. In this way, after the final injection device 10 is used, the active countdown timer is not removed until the expiry of one full countdown cycle, and may be continued if the correct type of injection device 10 is replenished before the countdown timer reaches zero.

The dosing time period for a type of injection device 10 represents the period of time required between each scheduled dosing time for the device type. The dosing time period for each injection device 10 may be recorded on the device tag 30 and transmitted to the device sensor 241. Alternatively, a dosing time period for one or more types of injection device 10 may be stored in the non-volatile memory 233 of the electronics system 200. The processor arrangement 230 may record the dosing time period for an injection device 10 in the device table based on the device information received from the device sensor 241.

The processor arrangement 230 generates an active countdown timer for each type of injection device 10 stored in the packaging assembly 100. Each active countdown timer is a countdown operation performed by the processor arrangement 230 as described above. The countdown time for each device type is initiated with the number of days specified by the dosing time period.

The expiry date of an injection device 10 represents the latest date on which the injection device 10 is considered suitable for use. When the expiry date is in the past the injection device 10 is considered to be expired and should not be used. The processor arrangement 230 records an expired flag when the expiry date of an injection device 10 is in the past.

Alternatively, the processor arrangement 230 may compare the expiry date of an injection device 10 with the next scheduled dosing time for the injection device 10. The processor arrangement 230 may already record an expired flag when the expiry date of the injection device 10 will pass before the next scheduled dosing time becomes due. The processor arrangement 230 may be further configured to record an expired flag if the injection device 10 is not suitable for use for any other reason. For example, if the internal temperature of the packaging assembly 100 is recorded as being too high for a predefined period of time, the processor arrangement 230 may record an expired flag for one or more injection devices 10 stored therein.

The electronics system 200 comprises a reset switch 215. The reset switch 215 is configured to provide a signal to the processor arrangement 230 when actuated by the reset button 164. The user presses the reset button 164 to indicate that an injection device 10 has been removed from the packaging assembly 100 and the medicament has been administered.

The reset switch 215 may be a mechanical switch mounted on the electronics system 200. The reset switch 215 is arranged to be actuated by the reset button 164. The reset switch 215 may be a normally open switch having an open state and a closed state. The reset switch 215 may be operated to move from the open state to the closed state when pressed. The reset switch 215 may be configured to pass a current in a closed state only. The reset switch 215 may be configured to provide a signal to the processor arrangement 230 when moved to the closed state.

The reset button 164 may be coupled to the reset switch 215. The reset switch 215 may be positioned below the reset button 164. If the reset button 164 is pressed, the reset switch 215 may be moved to the closed state by the reset button 164. The reset switch 215 is configured to provide a signal to the processor arrangement 230 when actuated by the reset button 164. The processor arrangement 230 may set the lid flag to have a value of 0 when the reset button 164 is pressed.

The processor arrangement 230 is configured to operate a reset timer. The processor arrangement 230 is configured to reset the time period for the next scheduled dosing time when the time period measured by the reset timer is over 2 seconds. The reset timer is started from zero when the reset switch 215 is moved to the closed state. Alternatively, the reset timer may be started at 2 seconds when the reset switch 215 is closed and count down such that the timer expires if the reset switch is not opened within 2 seconds.

The user must press and hold the reset button 164 for 2 seconds to maintain the reset switch 215 in the closed state for 2 seconds. The processor arrangement 230 filters out short presses of the reset button 164, so as to reduce the occurrence of falsely triggering the reset operation.

The electronics system 200 comprises the display 211 of the user interface 210. The display 211 can be operated to provide a notification. The display 211 can be operated to provide an indication of a status of the packaging assembly 100. The display 211 is an example of a status indicator. The display 211 can be operated to show information relating to the status of the packaging assembly 100. The display 211 can be operated to show any number from 00 to 99 by illuminating some or all of the LED segments. Certain letters may also be shown by the display 211.

The electronics system 200 may comprise a display driver 235. The display driver 235 may be provided as a separate integrated circuit chip to the processor arrangement 230, which is connected by an off-chip bus. Alternatively, the display driver 235 may be provided on a single integrated circuit chip with the processor arrangement 230. The display driver 235 may be a port expander for individually controlling the segments of a seven-segment LED display.

The processor arrangement 230 can operate the display 211 to show the number of days remaining until the next scheduled dosing time is due. The processor arrangement 230 is configured to determine the lowest active countdown timer, that is, the countdown timer with the fewest days remaining. The display 211 can be operated to show the number of days remaining on the lowest active countdown timer. The display 211 can be operated to provide a visual reminder output that the next scheduled dosing time is due. The display 211 can be operated further to provide a visual reminder output that the next scheduled dosing time is near.

For example, the processor arrangement 230 may start a new activate countdown timer from 14 days. If the countdown timer is the lowest, or only, active countdown timer, the display 211 is operated to show the number "14" to indicate that 14 days remain. Each day, the number of days shown by the display 211 is reduced by one. After 13 days, when 1 day remains until the scheduled dosing time, the display 211 is operated to show "01". The display 211 is operated to flash or blink to indicate that the scheduled dosing time is near. The display 211 is operated to flash by intermittently showing "01".

On the day of the scheduled dosing time, the display 211 is operated to show "00". The display 211 is operated to flash to indicate that the scheduled dosing time is due. The display 211 is operated to flash by intermittently showing "00". The flash periodicity of the display 211 may be of the order of 0.25 seconds to 2 seconds.

The processor arrangement 230 may check the state of charge of one or more batteries 170 included in the packaging assembly 100. If the state of charge is determined to be low, the display 211 may be operated to show a battery low warning.

The battery low warning shown by the display 211 may be a message comprising an upper case L on the first seven-segment array, and a lower case o on the second seven-segment array. That is, the display 211 may show the message "Lo". The battery low warning may be shown intermittently by the display 211 under the control of the processor arrangement 230. The display 211 may be operated to show the battery low warning alternately with the number of days remaining until the scheduled dosing time. The periodicity of the intermittent or alternating operation of the display 211 may be of the order of 0.25 seconds to 2 seconds The electronics system 200 comprises the LED array 220 of the user interface 210. The LED array 220 can be operated to provide a notification. LED array 220 can be operated to provide an indication of a status of the packaging assembly 100. The LED array 220 is an example of a status indicator.

The processor arrangement 230 can operate the LED array 220 to provide a visual reminder that a scheduled dosing time is due. On the day of a scheduled dosing time, the LED array 220 is operated to generate a visual reminder output. The processor arrangement 230 can operate the LED array 220 to provide a visual indication that an injection device 10 is expired. The processor arrangement 230 can operate the LED array 220 to provide a visual indication that an injection device 10 is not located in one of the openings 151. The processor arrangement 230 can operate the LED array 220 to provide a visual indication that the status of an injection device 10 is normal.

The LED array 220 comprises an array of eighteen light-emitting diodes (LEDs). The LEDs of the LED array 220 are arranged on the panel 150, in proximity to the openings 151. The LED array 220 comprises three LEDs 221,222,223 for each of the six openings 151. Each of the three LEDs 221,222,223 can be illuminated with a different colour. For example, the LED array 220 may comprise a blue LED 221, a white LED 222 and a red LED 223 for each opening 151.

The white LED 222 corresponding to an opening 151 is operated to provide a visual indication that the opening 151 is empty. When the device sensor 241 does not detect an injection device 10 located in the opening 151, the processor arrangement 230 records a value of NULL for the device ID in the device table. The white LED 222 is activated by the processor arrangement 230 when the corresponding entry in the device table has the value of NULL for the device ID.

The red LED 223 corresponding to an opening 151 is operated to provide a visual indication that the injection device 10 located in the opening 151 has expired. The red LED 223 is activated by the processor arrangement 230 when the corresponding entry in the device table has an expired flag.

The blue LED 221 corresponding to an opening 151 is operated to flash or blink to provide a visual reminder that the scheduled dosing time is due for the injection device 10 stored in the opening 151. When an active countdown timer indicates that a scheduled dosing time is due, the processor arrangement determines the device type associated with countdown timer. The processor arrangement 230 identifies the injection device 10 of the correct device type which has the earliest expiry date. If the identified injection device 10 is expired, the processor arrangement 230 determines the injection device 10 with the next earliest expiry date, until an injection device 10 is identified which is not expired. If the processor arrangement 230 identifies a plurality of injection devices 10 having the same device type and the same expiry date, then the injection device 10 having the lowest device index is identified. The processor arrangement 230 operates the blue LED 221 corresponding to the identified injection device 10 to flash or blink. The flash periodicity of the blue LED array 221 may be of the order of 0.25 seconds to 2 seconds.

The blue LED 221 corresponding to an opening 151 is operated to provide a visual indication that the injection device 10 located in the opening 151 has a normal status. If the injection device 10 is not expired, and a scheduled dosing time is not due, the blue LED 221 is illuminated continuously.

The electronics system 200 comprises the speaker 213 of the user interface 210. The speaker 213 can be operated to output a notification signal. The speaker 213 can be operated to provide an indication of a status of the packaging assembly 100. The speaker 213 is an example of a status indicator.

The processor arrangement 230 operated the speaker 213 to provide an audio reminder that the next scheduled dosing time is due. On the day of a scheduled dosing time, the speaker 213 is operated to output an audio reminder that the schedule dosage time is due. The speaker 213 may be operated to output an intermittent tone or tone sequence. The periodicity of the intermittent speaker 213 output may be of the order of 0.25 seconds to 2 seconds.

The processor arrangement 230 controls the operation of the speaker 213 according to the signal input by the lid open sensor 252. The processor arrangement 230 may control the operation of the speaker 213 according to the stored value of the lid flag. When the scheduled dosing time is due, the processor arrangement 230 operated the speaker 213 to output an audio indication that the scheduled dosing time is due, as described above. When the lid open sensor 252 provides a signal to the processor arrangement 230 to indicate that the lid 120 of the case 110 is open, the processor arrangement 230 controls the speaker 213 to deactivate the reminder.

When the lid open sensor 252 provides a signal to the processor arrangement 230 to indicate that the lid 120 is open, the processor arrangement 230 sets the lid flag to have a value of 1. The processor arrangement 230 controls the speaker 213 to deactivate the reminder when the stored value of the lid flag is equal to 1. The processor arrangement 230 resets the lid flag to have a value of 0 when the reset button 164 is pressed, so that the speaker 230 is activated when the next scheduled dosing time is due.

In this way, the audio reminder output by the speaker 213 is deactivated only when the lid opened by a user. The speaker 213 is deactivated only when the user opens the lid 120 of the case 110 to retrieve the injection device 10 for the scheduled dosage. The packaging assembly 100 thereby improves compliance with the scheduled dosage regime.

The processor arrangement 230 controls the display 211, LED array 220 and the speaker 213 according to an input from the fridge open sensor 251. If the fridge open sensor 251 indicated by signalling to the processor arrangement 230 that the fridge door is open, the processor arrangement 230 controls the display 211, LED array 220 and the speaker 213, as described above. If the fridge open sensor 251 does not indicate by signalling to the processor arrangement 230, the processor arrangement 230 does not activate the display 211, LED array 220 or the speaker 213.

In this way, the display 211, the LED array 220 and the speaker 213 are not active when the fridge is closed. The user interface 210 of the packaging assembly 100 is activated only when the fridge is open, therefore conserving the energy of the battery 170.

The processor arrangement 230 is configured to start the door timer from zero when the fridge door is opened. After the timer has been started, the device can be said to be in a door open state. The processor arrangement 230 is configured to enter a partial sleep state when the time period measured by the door timer is over 5 minutes. The display 211, LED array 220 and the speaker 213 are turned off by the processor arrangement 230 in the partial sleep state, and the processor arrangement operates at the stand-by clock speed.

Figure 7:
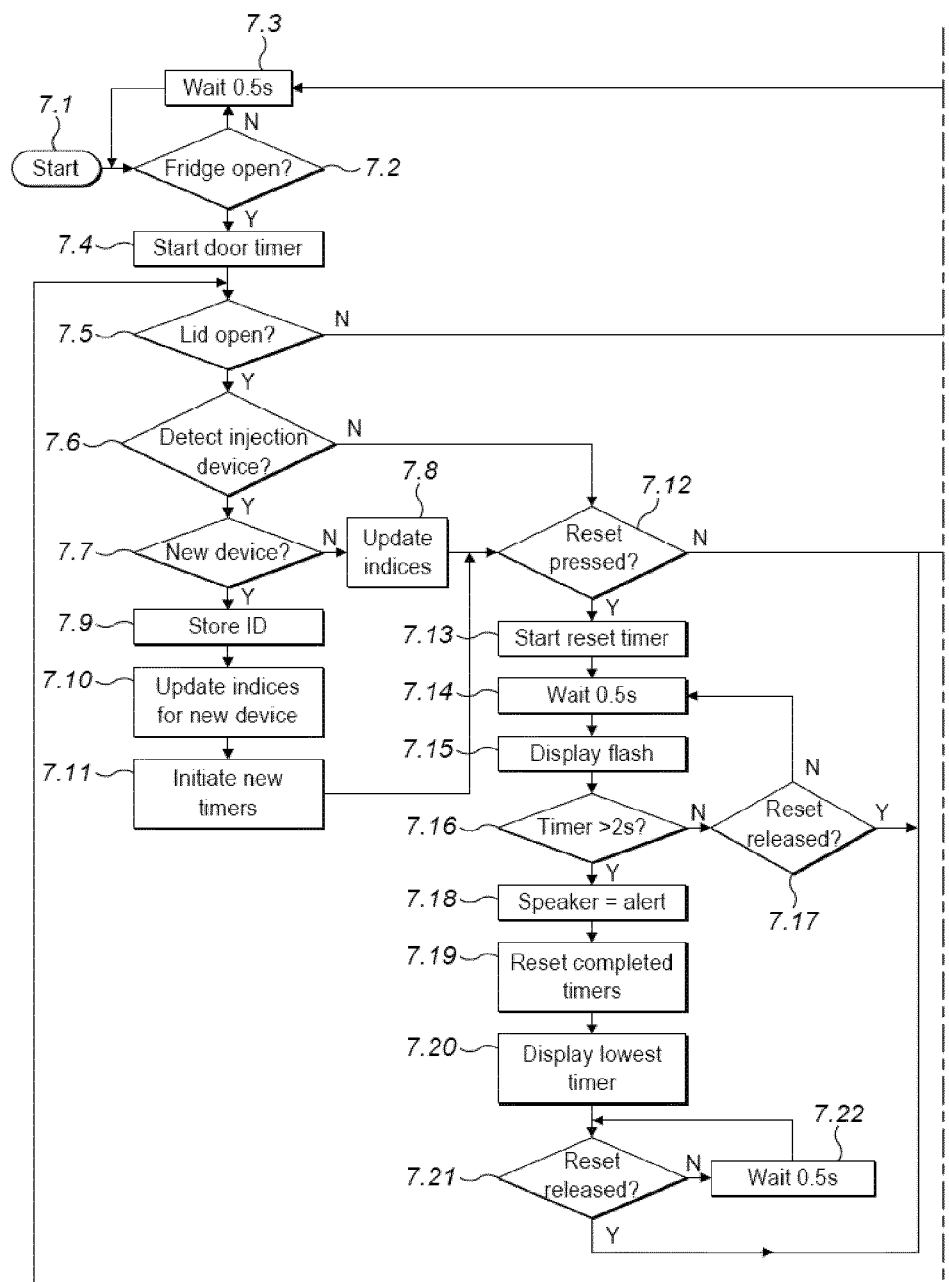
FIG. 7 is a flowchart illustrating a second exemplary operation of the packaging assembly, according to an exemplary embodiment.
Figure 7:
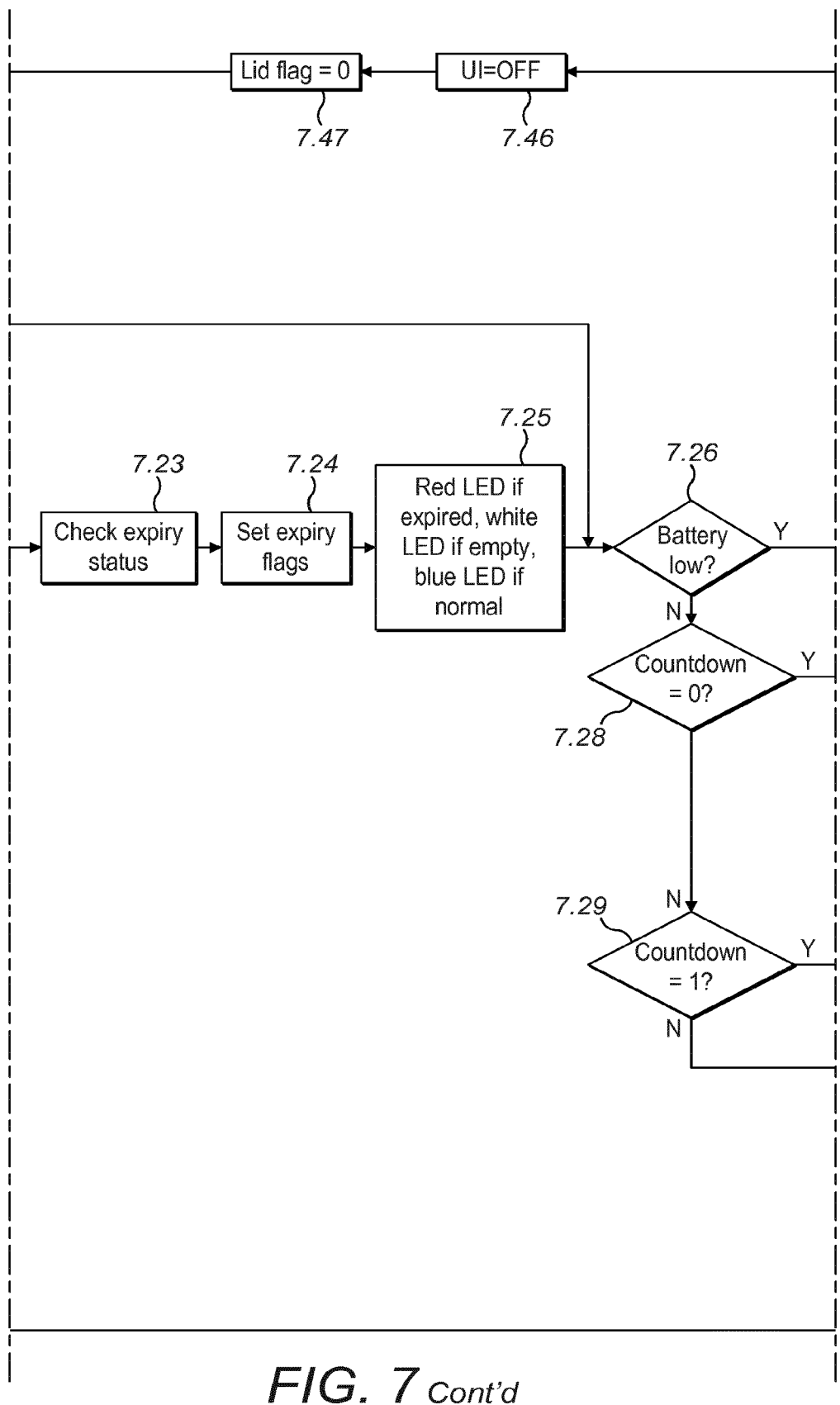
Figure 7:
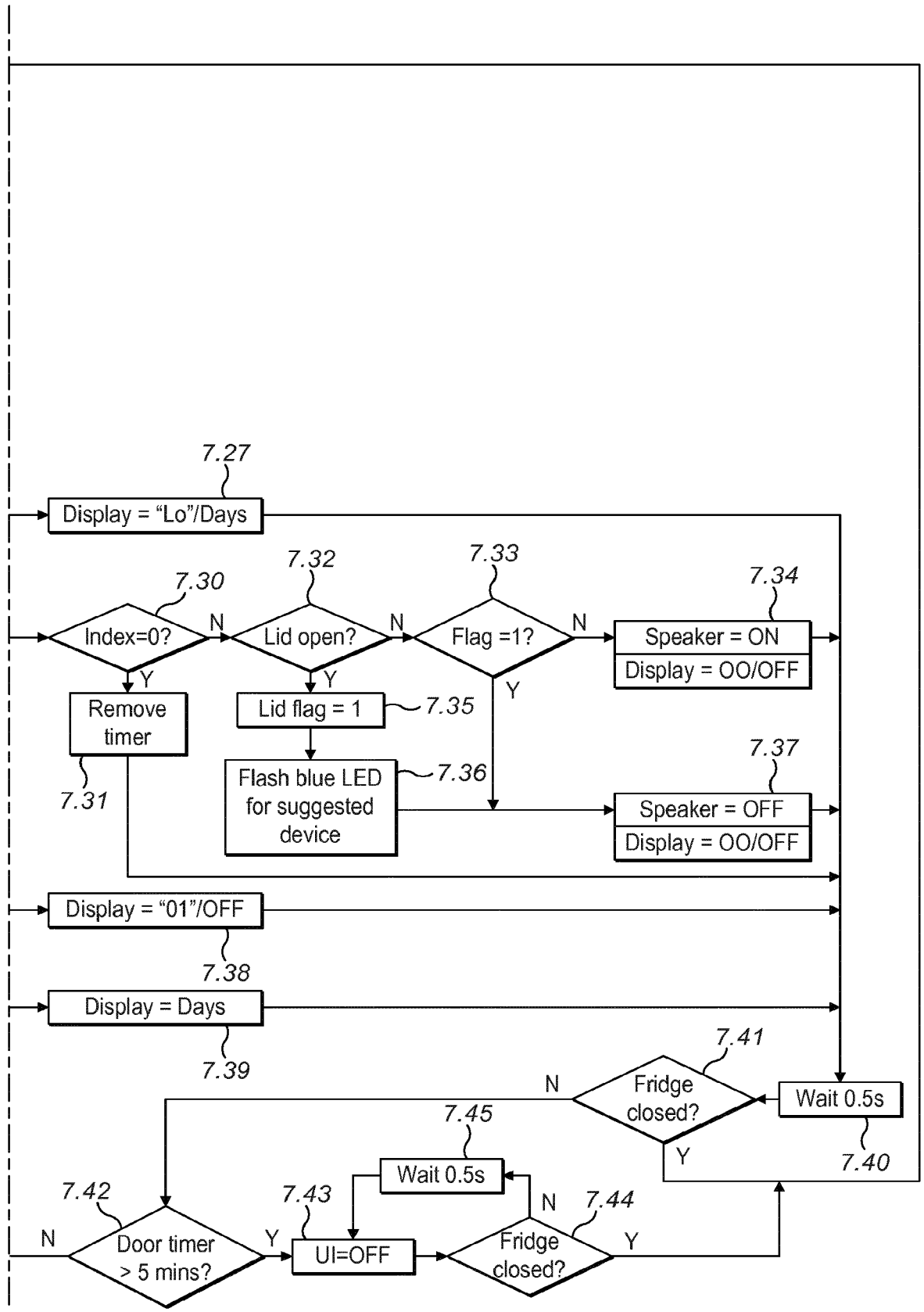

With respect to FIG. 7, a flowchart showing a second exemplary operation of the packaging assembly 100 is shown. The second exemplary operation of FIG. 7 supplements the first exemplary operation of FIG. 5. The second exemplary operation of FIG. 7 shows the first exemplary operation of FIG. 5 in a different manner, and includes more detail.

The Process Starts at Step 7.1.

At step 7.2, the processor arrangement 230 checks whether or not the fridge door is open. The processor arrangement 230 checks whether a signal to indicate that fridge door is open is received from the fridge open sensor 251. If a signal is not received, the processor arrangement 230 proceeds to step 7.3. At step 7.3 the processor arrangement 230 waits 0.5 seconds before returning to step 7.2 and checking again whether or not the fridge is open. If a signal indicating that the fridge door is open is received by the processor arrangement 230, the processor arrangement 230 proceeds to step 7.4. At step 7.4, the processor arrangement 230 starts a timer to monitor for how long the fridge door has been open.

At step 7.5, the processor arrangement 230 determines whether or not the lid 120 is open by checking whether or not a signal is received from the lid open sensor 252 to indicate that the hinge switch 252 is pressed by the actuating part 128 of the lid 120. If the processor arrangement 230 determines that the lid 120 is not open, the processor arrangement 230 proceeds to step 7.26. Otherwise, if the processor arrangement 230 determines that the lid 120 is open, the processor arrangement 230 proceeds to step 7.6.

At step 7.6, the processor arrangement 230 checks each of the device sensors 241 for the presence of an injection device 10. The processor arrangement 230 operates the sensor array 240 to determine whether or not a device tag 30 is located in proximity to any of the device sensors 241. An RF signal is transmitted by each of the plurality of device sensors 241. The processor arrangement 230 receives a signal from the sensor array 240 if a response signal is detected by a device sensor 241. In this case, the processor arrangement 230 proceeds to step 7.7. The processor arrangement 230 receives device information from the sensor array 240 if device information is received by a device sensor 241. If no signal is received from the sensor array 240, the processor arrangement proceeds to step 7.12.

At step 7.7, the processor arrangement 230 checks the device information received from the sensor array 240. The processor arrangement 230 checks the device ID for the detected injection device 10. If the received device ID is already stored in the device table, the processor arraignment 230 determines that the injection device 10 is being removed from the packaging assembly 100, and proceeds to step 7.8.

At step 7.8, the processor arrangement 230 updates the device table based on the removal of the injection device 10. If necessary, the processor arrangement 230 updates the device index for any injection devices 10 of the same device type. A device index for an injection device 10 may be reduced by 1 to replace an injection device which has been removed from the packaging assembly 100. The processor arrangement 230 further records a value of NULL in the device ID field for the entry of the device table corresponding to the removed injection device 10.

If the processor arrangement 230 determines at step 7.7 that the detected injection device 10 has a new device ID, the processor arrangement 230 proceeds to step 7.9.

At step 7.9, the processor arrangement 230 stores the device ID and device type for the injection devices 10 detected by the sensor array 240. The processor arrangement 230 receives the device ID and device type of the injection device 10 from the sensor array 240 and records the received device ID and device type in the volatile memory 232. The received device ID and device type for each opening 151 is recorded in the corresponding entry of the device table stored in the volatile memory 232.

At step 7.10, the processor arrangement 230 records device indices for entries in the device table which do not have a device index. A device index is generated and stored for each injection device 10 which is newly added to the packaging assembly 100. The device index is generated according to the device type of injection device 10, according to the number of injection devices 10 of the same device type which are already stored in the packaging assembly 100.

At step 7.11, the processor arrangement 230 creates a new timer for each newly added device type of injection device 10. The processor arrangement 230 checks the device type for each entry in the device table and, for each device type, checks that a corresponding countdown timer is active. For any device type which does not have an active countdown timer, the processor arrangement initiates a new countdown timer. A new countdown timer is initiated based on the time period for the device type stored in the device table.

At step 7.12, the processor arrangement 230 checks whether or not the reset button 164 has been pressed. The processor arrangement 230 is configured to reset the countdown timer to the scheduled dosing time only if the reset button 164 is held down for two seconds or more. If the processor arrangement 230 detects that the reset button 164 has been pressed, the processor arrangement 230 proceeds to step 7.13. At step 7.13, the processor arrangement 230 starts a reset timer to monitor for how long the reset button 164 has been pressed.

After starting the timer, the processor arrangement 230 proceeds to step 7.14 and waits 0.5 seconds. At step 7.15, the processor arrangement 230 operates the display 211 to flash on and off with the current number of days. Alternatively, the display 211 may show alternately the current number of days and a message to indicate that the reset operation is to be initiated. For example, the display 211 may show the message "—". If the reset button 164 is pressed at a scheduled dosing time, the display 211 shows "00" and "—" alternately. Further alternatively, the display 211 may alternately show the current number of days and the number of days in the dosing period for the countdown timer which is to be reset e.g. the display may show "00" and "14" alternately.

At step 7.16, the processor arrangement 230 checks whether or not the reset timer is over two seconds. If the reset timer is below two seconds, the processor arrangement 230 proceeds to step 7.17. At step 7.17, the processor arrangement 230 checks whether or not the reset button has been released.

If the reset button 164 is found to have been released before the reset timer has reached two seconds, then the processor arrangement 230 continues with the normal operation at step 7.23. If the reset button 164 has not been released, then the processor arrangement 230 returns to step 7.14 and waits 0.5 seconds before again checking the reset timer at step 7.16.

If the processor arrangement 230 finds that the reset timer is over two seconds, the processor arrangement 230 carries out a reset operation beginning with step 7.18. At step 7.18, the processor arrangement 230 operates the speaker 213 to output a short alert sound, to indicate to the user that the reset operation has been initiated.

At step 7.19, the processor arrangement 230 resets the countdown timer if it is completed. If multiple countdown timers are active and completed at the same time, the processor arrangement 230 may reset the countdown timer corresponding to the device type of the most recently removed injection device 10. The countdown timer is reset based on the timer period for the device type stored in the device table.

At step 7.20, the processor arrangement 230 operates the display 211 to show the number of days remaining for the lowest active countdown timer. The processor arrangement 230 checks each active countdown timer to determine which countdown timer has the fewest days remaining until expiry.

At step 7.21, the processor arrangement 230 checks whether or not the reset button 164 has been released. If the reset button 164 has been not been released, the processor arrangement 230 proceeds to step 7.22, and waits 0.5 seconds. The processor arrangement 230 then returns to step 7.21 and again checks whether or not the reset button 164 has been released. When the reset button 164 is determined to have been released, the processor arrangement 230 continues with the normal operation at step 7.23.

At step 7.23, the processor arrangement 230 checks the expiry condition for each injection device 10 stored in the packaging assembly 100. For each entry in the device table, the processor arrangement 230 checks the stored expiry date. If the stored expiry date is in the past, the processor arrangement 230 determines that the corresponding injection device 10 has expired.

At step 7.24, the processor arrangement 230 sets an expired flag for each expired injection device 10. The expired flag is recorded in the device table for each injection device 10 which is determined to be expired in step 7.23.

Alternatively, the processor arrangement 230 may compare the expiry date of an injection device 10 with the next scheduled dosing time for the injection device 10. The processor arrangement 230 may determine that the injection device 10 will expire before the next scheduled dosing time is due. The processor arrangement 230 may record an expired flag when the expiry date of the injection device 10 will pass before the next scheduled dosing time.

At step 7.25, the processor arrangement 230 controls the LED array 220 for each opening 151 according to the corresponding entry in the device table. If an entry in the device table shows an expired flag, the processor arrangement 230 operates the LED array 220 to activate the red LED 223. If the device ID of an entry in the device table shows that the opening 151 is empty, the processor arrangement 230 operates the LED array 220 to activate the white LED 222. The processor arrangement 230 operates the LED array 220 to activate the blue LED 221 for each opening 151 which contains an injection device 10 which is not expired. Where the condition of an injection device 10 is normal, the blue LED 221 is activated with a constant illumination.

At step 7.26, the processor arrangement 230 checks whether or not the battery 170 is low. If the battery 170 has a low state of charge, the processor arrangement 230 operates the user interface 210 to indicate this to the user.

The state of charge is determined to be low if it is below a defined threshold. The threshold may be built into the design of the packaging arrangement. The state of charge may be determined by measurement of the voltage provided by the battery 170, by monitoring energy use from a full state of charge, or a combination of these two techniques.

At step 7.27, the processor arrangement 230 operates the display 211 to show a battery low warning message alternately with the number of days on the countdown.

The battery low warning shown by the display 211 comprises an upper case L on the first seven-segment array, and a lower case o on the second seven-segment array. That is, the display 211 shows the message "Lo". For example, if the number of days on countdown to the scheduled dosing time is zero days, so the display 211 shows alternately the message "Lo" and the number zero ("00").

If the battery 170 does not have a low state of charge, the processor arrangement 230 checks the status of the lowest active countdown timer. First, at step 7.28, the processor arrangement 230 checks whether the countdown has reached zero days. If not, the processor arrangement 230 proceeds to step 7.29. At step 7.29, the processor arrangement 230 checks whether the countdown is at one day. If the countdown is not at zero days or one day, then the processor arrangement 230 determines that the countdown to the scheduled dosing time is greater than one day.

If the countdown to the schedule dosing time is zero days, then the processor arrangement 230 determines that the scheduled dosing time is due.

At 7.30, the processor arrangement 230 checks that the active countdown timer that has reached zero is still required. Where the scheduled dosing time for a certain device type is due, the processor arrangement 230 checks that at least one injection device 10 of that type is stored in the packaging assembly 100. The processor arrangement 230 checks the device indices stored for the device type in the device table. If no injection device 10 of the correct type is stored in the packaging assembly 100 the device index is "0". If the device index is "0" for more than the full countdown timer period for that device type, the processor arrangement 230 proceeds to step 7.31, and removes the countdown timer. If the device index at step 7.30 is not "0", the processor arrangement 230 proceeds to step 7.32.

At step 7.32, the processor arrangement 230 determines whether or not the lid 120 is open by checking whether or not a signal is received from the lid open sensor 252 to indicate that the hinge switch 252 is pressed by the actuating part 128 of the lid 120. If the processor arrangement 230 determines that the lid 120 is not open, the processor arrangement 230 proceeds to step 7.33.

At step 7.33, the processor arrangement 230 checks whether or not the stored value of the lid flag is equal to 1. The lid flag indicates whether or not the lid 120 has been opened. If the lid has not been opened, the value of the lid flag is 0. When the lid flag is not equal to 1, the processor arrangement 230 determines that the lid 120 has not been opened. When the lid flag is not equal to 1, the processor arrangement proceeds to step 7.34. At step 7.34, the processor arrangement 230 operates the speaker 213 to output a notification alert sound. The processor arrangement 230 operates the display 211 to flash the number of days, that is, zero days If the lid 120 is opened, the processor arrangement 230 determines at step 7.32 that the lid 120 is open. At step 7.35, the processor arrangement 230 sets a lid flag to have a value of 1. The lid flag indicates whether or not the lid 120 has been opened.

At step 7.36, the processor arrangement 230 operates the LED array 220 to activate the blue LED 221 for an opening 151 which contains an injection device 10 of the device type due for injection. The processor arrangement 230 determines the device type of injection device 10 corresponding to the countdown timer which has reached zero days. The processor arrangement 230 suggests the injection device 10 of the correct device type which is closest to expiry. The processor arrangement 230 determines the entry in the device table showing the earliest expiry date for the device type. The processor arrangement 230 activates the blue LED 221 for the opening 151 which corresponds to the determined entry. The processor arrangement 230 operates the blue LED 221 to blink.

If the entry showing the earliest expiry date for the device type is showing an expired flag, the processor arrangement 230 proceeds to the entry with the next earliest expiry date, until an injection device 10 which is not expired is identified. If the processor arrangement 230 identifies a plurality of injection devices 10 having the same device type and the same expiry date, then the injection device 10 having the lowest device index is identified. If an entry for the device type without an expiry flag is not available, the processor arrangement 230 may operate the red LED 223 of the corresponding opening 151 to blink. In this way, the user can be informed of the type of injection device 10 which is due for injection, when all of the stored injection devices 10 of this type have expired.

At step 7.37, the processor arrangement 230 deactivates the speaker 213. The processor arrangement 230 operates the display 211 to flash the number of days, that is, zero days.

In this way, a notification alert sound output by the speaker 213 can be deactivated only by the user opening the lid 120 to retrieve the required injection device 10. The packaging assembly 100 thereby improves compliance with the dosage regime.

If the lid 120 is closed, and the processor arrangement 230 determines at step 7.33 that the value of the lid flag is equal to 1, then the processor arrangement proceeds to step 7.37. At step 7.37, the processor arrangement 230 deactivates the speaker 213. The speaker 213 remains deactivated if the lid 120 is closed again after being opened.

If the number of days until the scheduled dosing time is one day, the processor arrangement 230 proceeds to step 7.38. At step 7.38, the processor arrangement 230 operates the display 211 to flash the number of days on the countdown. In this case, the display 211 flashes "01".

If the number of days until scheduled dosing time is greater than one day, the processor arrangement 230 proceeds to step 7.39. At step 7.39, the processor arrangement 230 operates the display 211 to show the number of days remaining.

The processor arrangement 230 thereby controls the output of the display according to the number of days remaining until the scheduled dosing time and according to the state of charge of the battery 170, and operates the speaker 213 according to whether or not the lid 120 of the case 110 is open.

After setting the output of the user interface 210, the processor arrangement 230 proceeds to step 7.40 and waits 0.5 seconds. The wait period while the fridge door is open may be shorter, to correspond to the normal processing clock speed when the device is in the door open state. The wait period and/or clock speed may be set based on the requirements for responsiveness and power consumption.

At step 7.41 the processor arrangement 230 checks whether or not the fridge door is closed. The processor arrangement 230 checks whether the signal to indicate that the fridge door is open is still being received from the fridge open sensor 251. If the processor arrangement 230 determines the fridge door is open, the processor arrangement 230 proceeds to step 7.42.

At step 7.42, the processor arrangement 230 checks the time currently on the door timer. The processor arrangement 230 checks whether or not the door timer is over five minutes. That is, the processor arrangement 230 checks whether the door of fridge has been open for more than five minutes. If the door of the fridge has been open for a period of less than five minutes, then the processor arrangement 230 returns to an earlier point of operation at step 7.5, immediately after the initial point of starting the door timer. The processor arrangement 230 again checks the reset button 164, checks the countdown until the scheduled dosing time, checks the state of charge of the battery 170, and checks the state of the lid 120 before setting the output of the user interface 210.

If the processor arrangement 230 determines that the door of the fridge has been open for a period longer than five minutes, the processor arrangement 230 controls the user interface 210 to enter a partial sleep state. At step 7.43, the processor arrangement 230 turns off the LED 220, the speaker 213, and the display 211, to conserve power. At step 7.44, the processor arrangement 230 checks again whether or not the fridge door has been closed. If the processor arrangement 230 determines that the fridge door is open, the processor arrangement 230 proceeds to step 7.45 and waits 0.5 seconds before returning to step 7.43.

If the processor arrangement 230 determines at step 7.44 that the fridge door has been closed, the processor arrangement 230 proceeds to step 7.46. At step 7.46, the processor arrangement 230 turns off the LED 220, the display 211 and the speaker 213. At step 7.47, the processor arrangement 230 sets the lid flag to have a value of 0, before returning to step 7.3, At step 7.3, the processor arrangement 230 waits 0.5 seconds before checking whether or not the fridge door has been opened, as described above.

This provides a door open timer that is activated in response to a determination of an intensity of light sensed by the light sensor rising above a defined threshold amount of light. The door open timer is cancelled in response to a determination of the intensity of light sensed by the light sensor falling below the threshold amount of light, which corresponds to the door being closed. If the time expires before it is cancelled, it is determined that the fridge door has been left open unintentionally and optical and audio alerts and visual indications of remaining time to day zero are suppressed. This reduces power consumption of the device with relatively little reduction in useful alerting. Once the fridge door is shut again, normal operation resumes. When subsequently the fridge door is again opened, alerting and indication occurs as usual in the door open mode.

Figure 8:
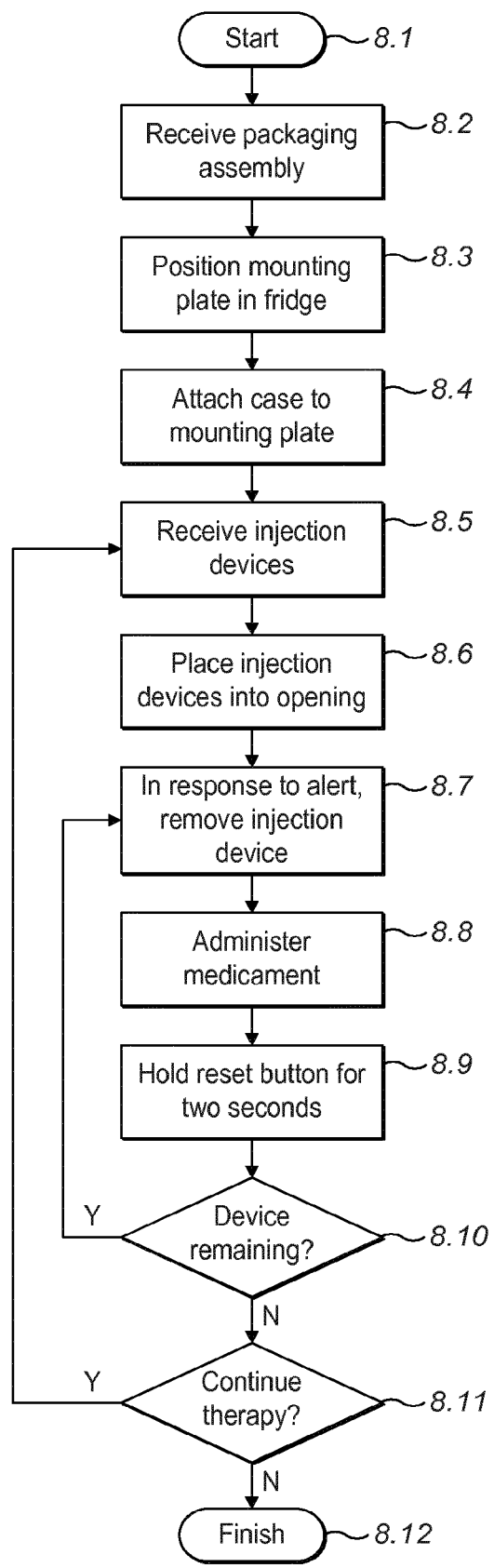
FIG. 8 is a flowchart illustrating an exemplary user operation of the packaging assembly according to any embodiment.

A first exemplary user operation of the packaging assembly 100 will now be described with respect to FIG. 8.

The Operation Starts at Step 8.1.

At step 8.2, the user receives the packaging assembly 100. The packaging assembly 100 may be empty. The packaging assembly 100 may include one or more batteries 170. Alternatively, the user may insert batteries 170 into the battery opening 145.

At step 8.3, the mounting plate 190 is fixed to an internal surface of the fridge using the adhesive strips 191.

At step 8.4, the case 110 of the packaging assembly 100 is attached to the mounting plate 190 by magnets 148. The empty packaging assembly 100 may be placed in the fridge until the internal temperature of the case 110 has been cooled to reach the temperature of the fridge.

At step 8.5, the user receives a plurality of injection devices 10. The user may receive up to six injection devices 10, of any type, for storage in the packaging assembly 100.

At step 8.6, the user places the injection devices 10 into the openings 151 of the packaging assembly 100. As each injection device 10 is inserted into an opening 151, the device sensor 241 corresponding to the opening 151 detects the device tag 30 of the injection device 10. The sensor array 240 receives the device information from the newly inserted injection device 10 and updates the device table accordingly.

An active countdown timer is set by the processor arrangement 230 for each new device type of injection device 10 inserted into the packaging assembly 100. The time period for each active countdown time is set according to the device type. The user can now use the fridge as normal until the next scheduled dosing time is due.

When the next scheduled dosing time is due, the user is provided with a reminder alert upon opening the fridge. The user may be provided with a visual reminder alert. The user may be provided with an audio reminder alert.

At step 8.7, in response to the reminder alert, the user removes an injection device 10 from the packaging assembly 100. The audio reminder alert is deactivated when the lid 120 of the packaging assembly 100 is opened.

At step 8.8, the user administers the medicament using the injection device 10.

At step 8.9, the user holds the reset button for at least 2 seconds. The processor arrangement 230 resets the active countdown timer which has reached zero, and the reminder alert is deactivated.

At step 8.10, the user checks the number of injection devices 10 remaining in the packaging assembly 100. If there is at least one injection device 10 in the packaging assembly 100, the user returns to step 8.7. The user continues to use the fridge as normal until the next scheduled dosing time is due.

If there are no injection devices 10 remaining in the packaging assembly 100, at step 8.11, the user determines whether the therapy is to be continued. If yes, the user obtains or receives a further batch of injection devices 10, and the operation continues from step 8.5. If not, the operation finishes at step 8.12. When the next scheduled dosing time is due, if the packaging assembly 100 has not been refilled, the processing arrangement 230 removes the active countdown timer and the operation terminates.

Figure 9:
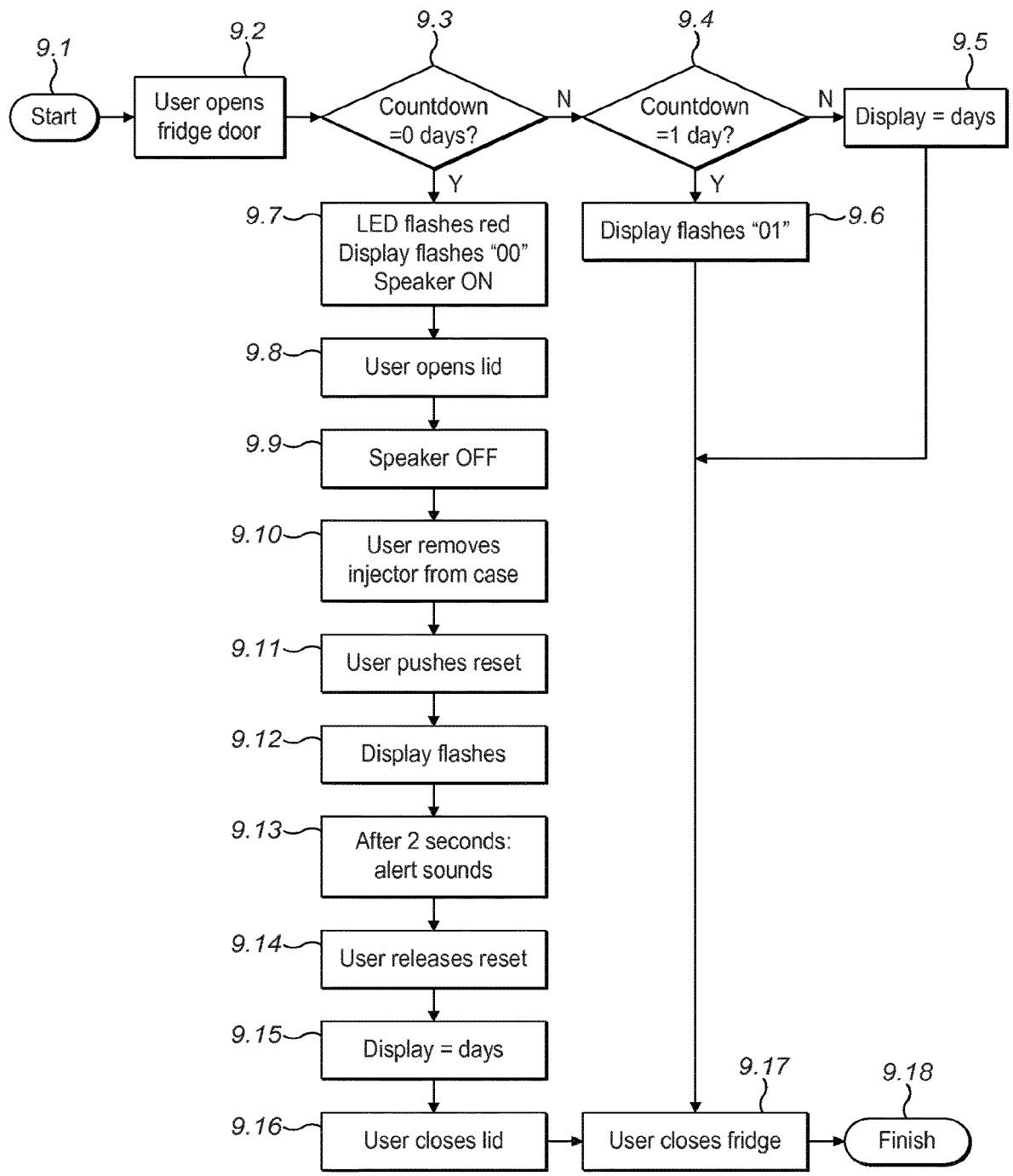
FIG. 9 is a flowchart illustrating an exemplary user operation of the packaging assembly according to any embodiment.

With respect to FIG. 9, a flowchart showing a second exemplary user operation of the packaging assembly 100 is shown. The second exemplary user operation of FIG. 9 supplements the first exemplary user operation of FIG. 8. The second exemplary user operation of FIG. 9 shows a part of the first exemplary user operation of FIG. 8 in a different manner, and includes more detail.

The Operation Starts at Step 9.1.

At step 9.2, the user opens the fridge door. The user may open the fridge door specifically to check the packaging assembly 100, or as part of their daily routine. The user may be taking food from the fridge or placing food into the fridge.

If the number of days remaining on the lowest active countdown timer is greater than 1 day, then the countdown timer is not equal to 0 days at step 9.3 and the operation proceeds to step 9.4, The lowest active countdown timer is not equal to 1 day and the operation proceeds further to step 9.5.

At step 9.5, the display 211 shows the number of days remaining until the next scheduled dosing time. The user can see the static blue light of the display 211 through the translucent lid 120. The user can read the display through the viewing window 121. The display 211 shows the number of days remaining on the lowest active countdown timer. The number of days is shown until the user closes the fridge door at step 9.17. For the purpose of this illustration, it is assumed that the user closes the fridge door within 5 minutes of it being opened, so the display and audio alert suppression is not provided.

If the number of days remaining until the next scheduled dosing time is 1 day, then the lowest active countdown timer will be determined to be equal to 1 day at step 9.4, and the operation proceeds to step 9.6.

At step 9.6, the display 211 flashes the number of days remaining until the next scheduled dosing time. That is, the display 211 flashes "01". The user can see the flashing blue light of the display 211 through the translucent lid 120. The user can read the display 211 through the viewing window 121. The number "01" is flashed until the user closes the fridge at step 9.17.

If the number of days remaining until the next scheduled dosing time is 0 days, then the lowest active countdown timer will be determined to be equal to 0 days at step 9.3, and the operation proceeds to step 9.7.

At step 9.7, the display 211 flashes the number "00" and the speaker 213 outputs an intermittent tone or tone sequence. The user can see the flashing blue light of the display 211 through the translucent lid 120. The user can read the display 211 through the viewing window 121. The user can hear the intermittent tone or tone sequence output by the speaker 213.

At step 9.8, the user opens the lid 120 of the packaging assembly 100.

At step 9.9, the speaker 213 is turned off. The speaker 213 is turned off in response to the lid 120 being moved from a closed position to an open position. The blue LED 221 flashes for the opening 151 which contains the injection device 10 to be used. The user can see the flashing blue LED 221 and determine which injection device 10 is to be used next.

At step 9.10, the user removes the injection device 10 from the packaging assembly 100 out of the suggested opening 151. The device table is updated according to the device information gained from device tag 30 of the removed injection device 10.

At step 9.11, the user pushes the reset button 164. The user holds down the reset button 164.

At step 9.12, the display 211 flashes in response to the reset button 164 being pushed, The display may flashes "—" alternately with the current number of days until the scheduled dosing time or, alternatively, the display may flash between e.g. "14" and "00", as described above.

At step 9.13, after the reset button 164 has been held for 2 seconds, the speaker 213 outputs a simple alert sound and the countdown timer is reset.

At step 9.14, the user releases the reset button 164.

At step 9.15, the display 211 shows the number of days remaining until the next scheduled dosing time. The display 211 shows the number of days remaining on the lowest active countdown timer.

At step 9.16, the user closes the lid 120.

At step 9.17, the user closes the fridge door.

The operation finishes at step 9.18.

Figure 10A:
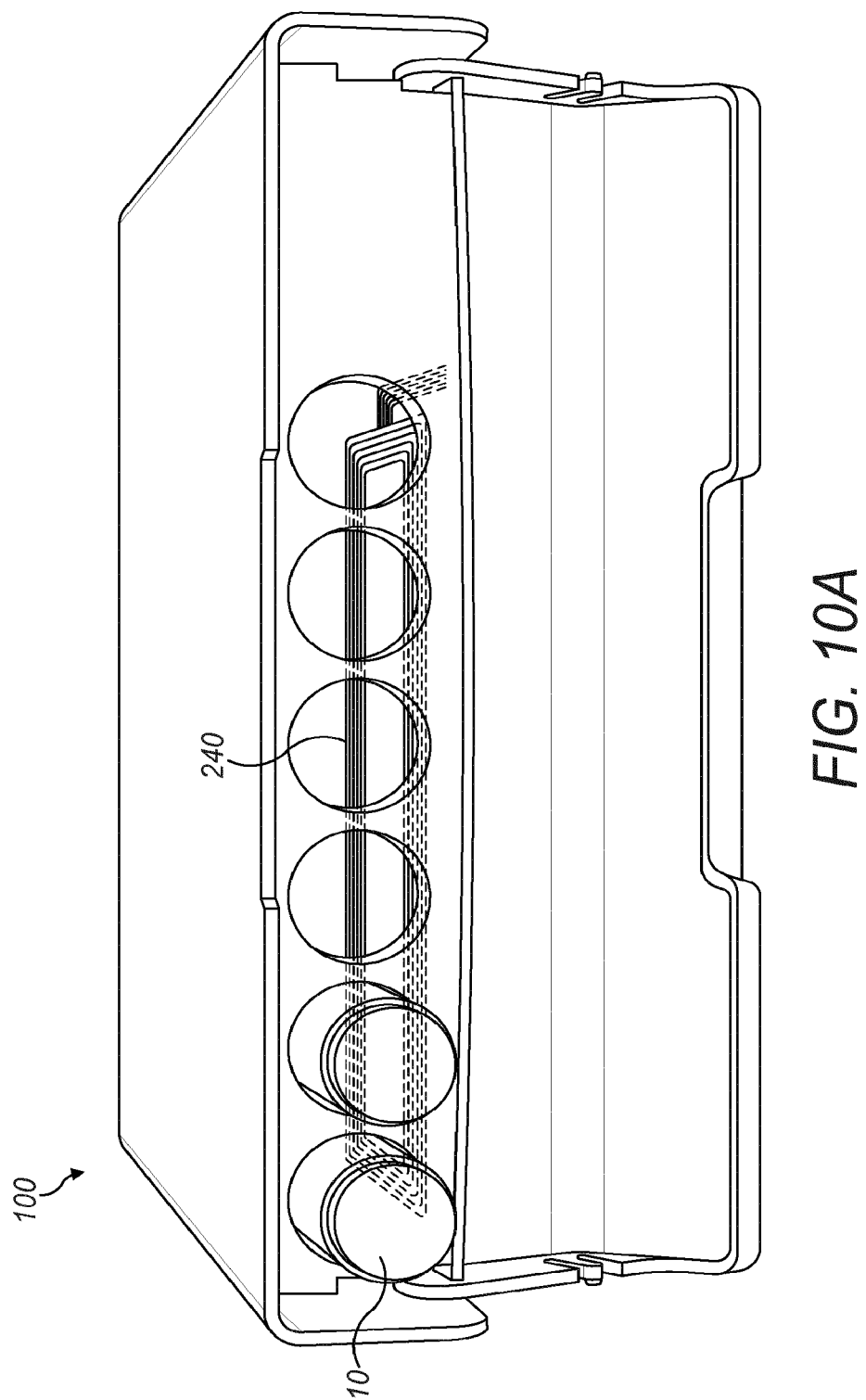
FIG. 10A is a front section view illustrating a packaging assembly according to an exemplary embodiment.

With respect to FIG. 10A, a packaging assembly 100 according to an exemplary embodiment is shown. Elements of the electronic system 200 and the user interface 210 are omitted for visual clarity. Elements not described below are substantially the same as those of the first embodiment.

The sensor array 240 comprises a single device sensor. The sensor array 240 is a radio-frequency identification (RFID) reader comprising a radio-frequency antenna. The sensor array 240 extends across the full width defined by the plurality of openings 151. The sensor array 240 is formed as a wire extending rearwards from the PCB 201 (not shown) and forming a horizontal loop. The sensor array 240 is arranged adjacent to the base of the case 110, below the plurality of injection devices 10 stored in the case. Alternatively, the sensor array 240 may be positioned above the plurality of injection devices 10. The sensor array 240 is arranged at a forward end of the case 110, immediately behind the PCB 201.

The sensor array 240 is arranged to detect a device tag 30 of an injection device 10 as the injection device 10 is passed through one of the openings 151. The sensor array 240 generates an electromagnetic field at a forward end of the case 110, immediately behind the openings 151. An injection device 10 passed through any of the plurality of openings 151 passes through the field generated by the sensor array 240. A specific opening 151 in the plurality of openings 151 in which the injection device 10 is inserted can be identified from the signal runtime, the signal from a specific opening further from the PCB will have a longer signal runtime than that of a specific opening closer to the PCB. When an injection device 10 is fully in position within the case 110, the device tag 30 is displaced from the field of the sensor array 240.

Figure 10B:
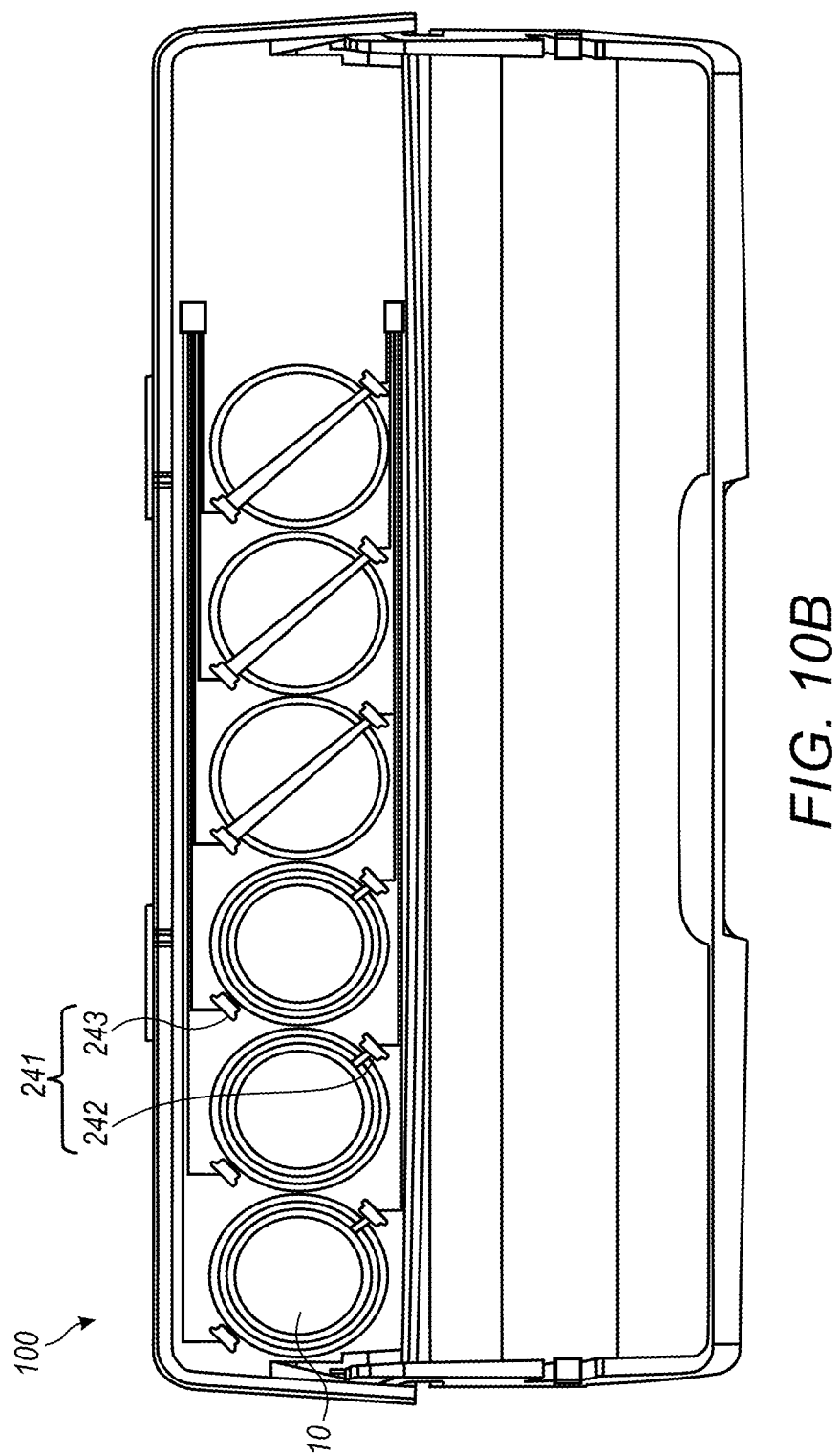
FIG. 10B is a front projection view illustrating a packaging assembly according to an exemplary embodiment.

With respect to FIG. 10B, a packaging assembly 100 according to an exemplary embodiment is shown. Elements of the electronic system 200 and the user interface 210 are omitted for visual clarity. Elements not described below are substantially the same as those of the first embodiment.

The sensor array 240 comprises a plurality of device sensors 241. Each of the device sensors 241 is formed as a light gate comprising a light source 242 and a photo-detector 243. The light source and photo-detector are arranged in opposition across one of the openings 151. A light gate is formed across each of the plurality of openings 151. The device sensors 241 determine whether or not an injection device 10 is positioned in each opening, according to whether or not the light from the light source is received by the photo-detector. The light source may be, for example, an LED or a laser.

Figure 10C:
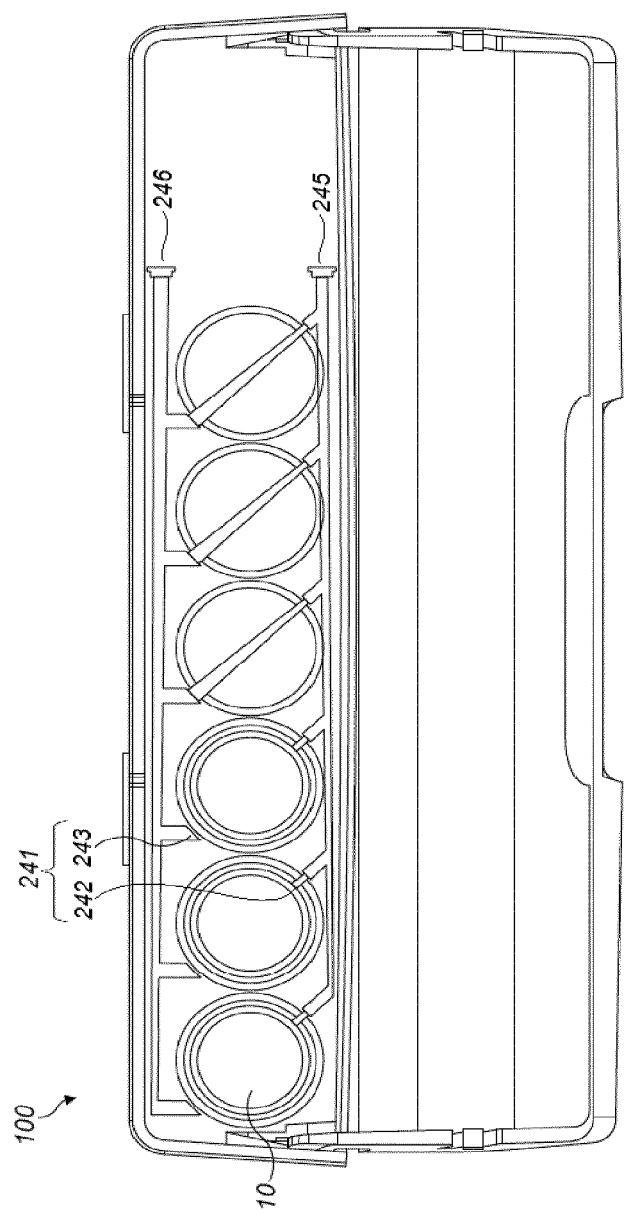
FIG. 10C is a front projection view illustrating a packaging assembly according to an exemplary embodiment.

With respect to FIG. 10C, a packaging assembly 100 according to an exemplary embodiment is shown. Elements of the electronic system 200 and the user interface 210 are omitted for visual clarity. Elements not described below are substantially the same as those of the first embodiment.

The sensor array 240 comprises a plurality of device sensors 241. Each of the device sensors 241 is formed as a light gate across each of the plurality of openings 151. The sensor array 240 comprises a single light source 245 and a single photo-detector 246. The light source may be, for example, an LED or a laser. An output optical guide is arranged to direct light emitted by the light source to each of the plurality of openings 151. An input optical guide is arranged to direct light from each of the plurality of openings 151 to the photo-detector. Each of the input optical guide and the output optical guide is formed by, for example, an optical fibre structure.

A light gate is formed across each of the plurality of openings 151. The device sensors 241 determine whether or not an injection device 10 is positioned in each opening, according to whether or not the light from the light source is received by the photo-detector. The input optical guide may direct the light from each device sensor 241 to a different part of the photo-detector, such that the sensor array 240 can determine which of the openings 151 is filled, according to the position of the received light. Alternatively, the sensor array 240 may determine which openings are occupied based on the frequency and/or intensity of the received light, based on the optical properties of the output optical guide and input optical guide. Alternatively the sensor array 240 may determine which openings are occupied based on signal chopping. Signal chopping periodically splits the signal so that the light reaches one specific opening in the plurality of openings 151 at a given instance, combined with a clock the specific occupied opening can be identified.

Figure 11A:
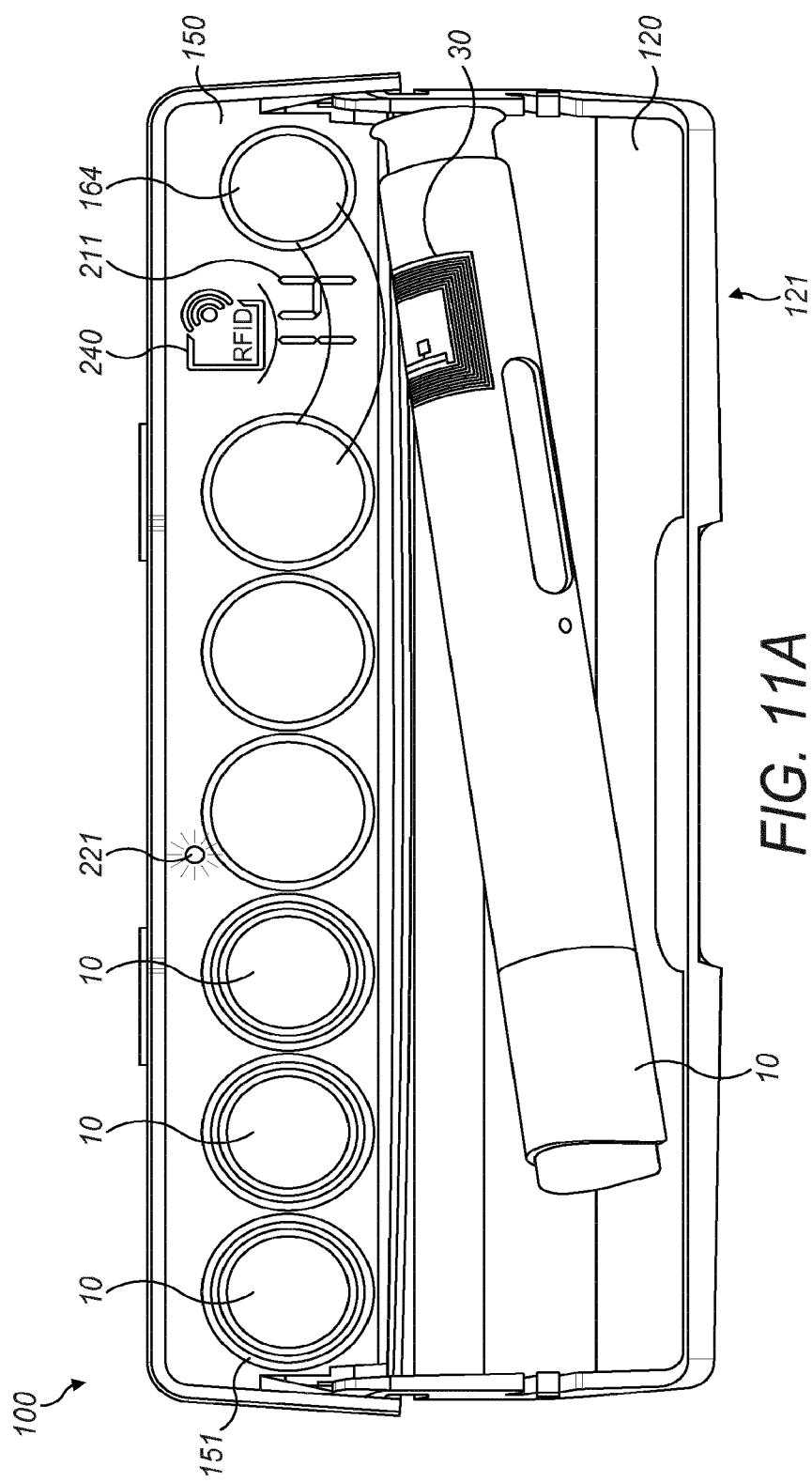
FIG. 11A is a front projection view illustrating a packaging assembly according to an exemplary embodiment.

With respect to FIG. 11A, a packaging assembly 100 according to an exemplary embodiment is shown. Elements not described below are substantially the same as those of the first embodiment.

The sensor array 240 comprises a single device sensor. The sensor array 240 is a radio-frequency identification (RFID) reader comprising a radio-frequency antenna. The sensor array 240 is mounted on or immediately behind the panel 150. The sensor array 240 generates an electromagnetic field in front of the panel 150, and detects a response signal from a device tag 30 which is passed through the field.

The user presents the device tag 30 of each injection device 10 to the sensor array 240 as the injection device 10 is added to or removed from the packaging assembly 100. As shown, the blue led 221 is flashing to indicate that the scheduled dosing time is due. The user removes the injection device 10 from the opening 151 and presents the device tag 30 to the sensor array 240, before the medicament is administered. After administration of the medicament, the reset button is pushed, as normal. In the case of adding an injection device 10 to the packaging assembly 100, a flashing white LED may indicate which empty opening 151 the injection device 10 should be inserted into.

The RFID reader of the sensor array 240 may be combined with a plurality of light gates to indicate the occupancy of each opening 151, as shown in either of FIG. 10B or 10C.

Figure 11B:
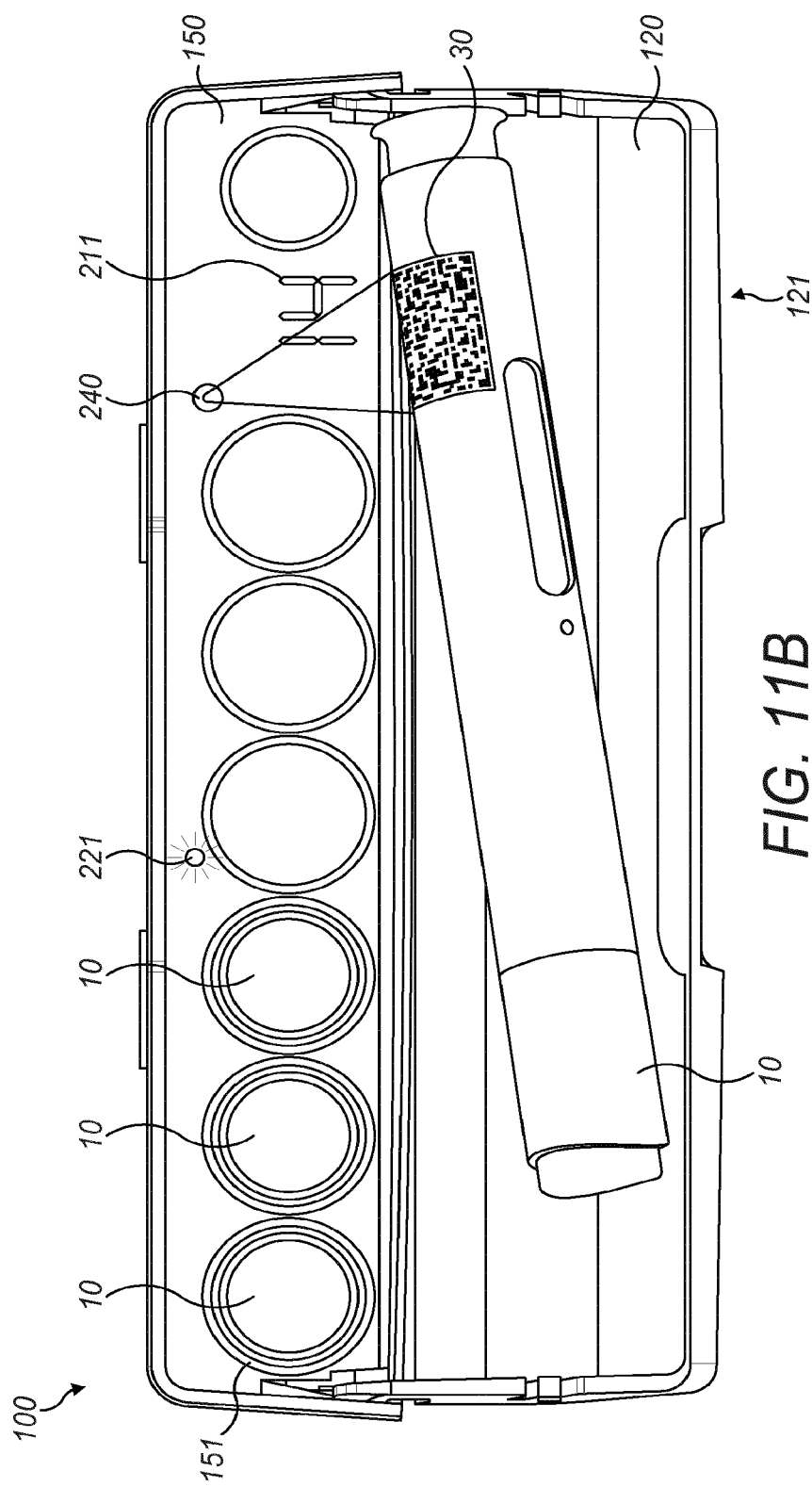
FIG. 11B is a front projection view illustrating a packaging assembly according to an exemplary embodiment.

With respect to FIG. 11B, a packaging assembly 100 according to an exemplary embodiment is shown. Elements not described below are substantially the same as those of the first embodiment.

The sensor array 240 comprises a single device sensor. The sensor array 240 is an optical sensor, e.g. a barcode reader, comprising a light source and a photo-detector. The sensor array 240 is mounted on the panel 150. The sensor array 240 is configured to detect and read an optical label such as a barcode or quick response (QR) code.

The device tag 30 of each injection device 10 comprises a QR code. The user presents the device tag 30 of each injection device 10 to the sensor array 240 as the injection device 10 is added to or removed from the packaging assembly 100. As shown, the blue led 221 is flashing to indicate that the scheduled dosing time is due. The user removes the injection device 10 from the opening 151 and scans the device tag 30 using the sensor array 240, before the medicament is administered. After administration of the medicament, the reset button is pushed, as normal. In the case of adding an injection device 10 to the packaging assembly 100, a flashing white LED may indicate which empty opening 151 the injection device 10 should be inserted into.

The RFID reader of the sensor array 240 may be combined with a plurality of light gates to indicate the occupancy of each opening 151, as shown in either of FIG. 10B or 10C.

It will be appreciated that the above described embodiments are purely illustrative and are not limiting on the scope of the claims. Other variations and modifications will be apparent to persons skilled in the art upon reading the present application, and some will now be described.

The case of the packaging arrangement may be a generally rectangular shape or may be any other shape suitable for containing the plurality of injection devices. The case may be a suitable shape and size for placement within a household refrigerator.

The case may be formed to enclose the injection devices and may be sealed, Alternatively, the case may be formed as a structure for supporting the plurality of injection devices externally. The injection devices may be arranged in one or more rows, e.g. a row of six or two rows of three, or in a circular arrangement. The injection devices may be arranged to hang below a supporting structure or to be placed on top of the supporting structure.

The case may be configured to store any number of injection devices, according to the dosage requirements of the medicament. For example, the case may store between 5 and 15 injection devices. Case may be sized to store enough injection devices for one quarter, or for a 6 month period. Where medicament is administered more regularly, the case may store enough injection device s for one week.

The case may be formed of an opaque material. One or more of the components of the case may be formed with at least a transparent portion. A transparent portion of the case may allow the user to see the number of injection devices, or to see the user interface. One or more components of the case may be translucent to improve visibility of a visual reminder output.

The case may be formed of a plastics material such as polyethylene, polystyrene, polycarbonate, or it may be made of any other suitable material. Desired properties for the material of the case include temperature stability, moderate impact strength, resistance to cleaning fluids, a wipe-clean finish, and rigidity.

Each part of the case may be formed in a single piece e.g. a moulded plastic part. Alternatively, parts may be machined. The body of the case may be formed from two parts joined or attached together, or may be formed in a single part. An internal of the case may be formed as a single large cavity, a cavity divided into a plurality of areas for holding each injection device, or may be formed as a plurality of cavities for individually holding each injection device.

The case may comprise any number of magnets sufficient to support the weight of the packaging arrangement and injection devices. For example, the case may include 2 larger magnets or an arrangement of 6 smaller magnets. The magnets may be any permanent magnets and may be rare earth magnets. The magnets may be formed of neodymium or may be formed of samarium cobalt.

The case may further comprise one or more ventilating apertures to allow air flow into the case. Alternatively, the case may be sealed when the lid is in a closed position. The lid may further comprise a rubber seal to prevent air passing into the case between the lid and the case. The case may be insulated to maintain the low temperature of the injection devices if removed from the fridge for a short period of time.

The lid may be coupled to the case with a hinge. The mechanism for connecting the lid to the case and for allowing the lid to open and close may take any suitable form. Instead of the hinge mechanism described above, the hinge may be a butt hinge, a living hinge or some other type. The lid may be coupled to the case with a flexible and/or elastic material. The hinge may allow some translational movement as well as pure rotational movement, to allow better viewing of or access to the internal part of the case when the lid is open.

The hinge may allow the removal of the lid by a user. For instance, the protrusions of each of the second hinging parts may be pushed inwards to disengage from the respective first hinging parts and decouple the lid from the case. The user may be provided with one or more alternative lids which may be a different design, for example, a different colour. An alternative lid may have a larger transparent portion or may be entirely opaque.

Alternatively, the lid may slidably engage with the case. The lid may comprise runners at the edges, each configured to engage with a corresponding groove on the case. The lid may slide out of the grooves and decouple from the case. The lid may be arranged to slide to the limit of the grooves and pivot freely in the open position. Further alternatively, the lid may be separate from the case and fixedly attached thereto with a friction fit. The lid may fit tightly within the opening at the upper end of the case, or may fit over an upper portion of the case.

The lid may comprise a latch to maintain the lid in the closed position. The latch may comprise a sliding catch arranged to slidably move between a first position and a second position. The catch may be arranged to protrude from an edge of the lid in the first position. The catch may be configured to slidably retract to not protrude in the second position. The latch may comprise a spring to urge the catch to the first position. The catch may be configured to engage with an opening in the case in the first position when the lid is in the closed position. The catch may engage with the opening to maintain the lid in the closed position.

The latch may be a sprung push-catch push-release mechanism. The latch may be configured to engage with a first push into the closed position and maintain the lid in the closed position. The latch may be configured to disengage with a second push and allow the lid to open. The latch may be configured to engage when the lid is closed to hold the lid in the closed position. The latch may further comprise a release switch to disengage the latch and allow the lid to open. The release switch may be a mechanical switch or an electric switch. The release switch may be an electric switch coupled to a code input, which is configured to disengage the lid catch when a correct code is entered.

Although the lid open sensor is described as an electro-mechanical switch, it may instead be an optical sensor arrangement, a magnetic sensor arrangement or any other suitable arrangement that is configured to detect whether the lid is open or closed or whether the lid is transitioning from a closed position to an open position.

The packaging assembly may comprise a case without a lid. The packaging assembly may not include a lid open sensor. The speaker may instead be deactivated by the processor arrangement according to an alert timer. The processor arrangement may be configured to operate the alert timer. The processor arrangement may activate the alert timer when the speaker is controlled to output an audio reminder alert that the scheduled dosing time is due. The processor arrangement may activate the alert timer when the scheduled dosing time is due, conditional on the fridge door being open. The processor arrangement may deactivate the speaker when the alert timer reaches 30 seconds. Alternatively, the processor arrangement may activate the alert timer at 20 seconds and count down until the timer expires. The processor arrangement may be configured to deactivate the speaker when the alert timer expires. The expiry time period for the alert timer may be 5 seconds to 60 seconds.

The electronics system may include a device sensor to determine whether an injection device is positioned in one of the plurality of openings. The device sensor may determine whether an injection device is positioned within each of the openings. The processor arrangement may be configured to deactivate the speaker when the device sensor indicates that an injection device has been removed from an opening.

The device sensor may comprise one or more device switches. The device switches may be arranged respectively within the openings. Each device switch may be a mechanical switch. The device switch may be a normally open switch which is pressed to a closed position by an injection device when in position in the opening. The device switch may be a membrane switch. The device switch may be actuated by a lever located within the opening.

Each device switch may be configured to send a signal to the processor arrangement when an injection device is located within the corresponding opening. The processor arrangement may be configured to activate or deactivate the speaker when a signal is no longer received from a device switch. The processor arrangement may be configured further to reset the countdown to the scheduled dosing time when an injection device is removed from the opening. Alternatively, where an injection device is replaced in the case after the dose is administered, the processor arrangement may be configured to reset the countdown when the injection device is replaced. The processor arrangement may be configured to monitor the number of injection devices in position in the packaging assembly. The processor arrangement may control the display to show the number of injection devices in the packaging assembly. The processor arrangement may control the electronics system to provide a notification output when the packaging assembly is empty.

The retention mechanism may be arranged at the lower end of the case. The retention mechanism may be arranged to engage with the end of each injection device which is passed through the opening. The retention mechanism may comprise a further plurality of openings at the lower end of the case. The further openings may be sized so as to hold the injection devices in position with a friction fit. Alternatively, the retention mechanism may comprise a levered pincer arrangement arranged to grip the sides of an injection device when the injection device is pushed longitudinally into the arrangement, and to release the injection device when the injection device is pulled longitudinally out of the arrangement.

The retention mechanism may comprise a release switch configured to disengage the retention mechanism. The release switch may be configured to release one or all of the injection devices. A plurality of release switches may be provided for the corresponding plurality of injection devices. The release switch may be a mechanical switch or lever coupled to the retention mechanism. The release switch may be further coupled to an ejection mechanism. The release switch may be an electromechanical switch. The release switch may be controlled by the processor arrangement. The processor arrangement may control the release switch to disengage the retention mechanism conditional on the scheduled dosing time being due. The processor arrangement may control the release switch to disengage the retention mechanism for one injection device when the scheduled dosing time is due.

The ejection mechanism may comprise one or more springs arranged to push a portion of the respective injection devices out of the corresponding openings. The ejection mechanism may be biased against the retention mechanism to push each injection device when released by the retention mechanism. The retention mechanism may be controlled to release one injection device, which is pushed partially out of the opening by the ejection mechanism. This arrangement may provide a visual reminder alert in the form of a portion of the injection device being pushed out of the opening.

Alternatively, the ejection mechanism may comprise a motorised actuator. For example, a roller arranged perpendicularly to the plurality of injection devices may be driven to push the injection devices out of the openings. The roller may push all of the injection devices equally, with the retention mechanism configured to hold all but one of the injection devices in position. Further alternatively, the actuator may comprise a protruding part from the rear of the case which is driven laterally across the width of the case. The protruding part may be driven along a rail, or may protrude from a belt extending along the width of the case. The protruding part is configured to engage with each injection device in turn and push the injection device out of the opening.

The time period for a reminder may be any suitable dosing period, dependent upon the medicament which is stored in the packaging assembly. The time period set until the next scheduled dosing time may be any number of days and may be, for example, between 2 and 60 days. The time period may be a number of weeks, for example, a period of 7 days, 14 days, 21 days or 28 days. The time period may be 28 days, which is 4 weeks, or the time period may be 1 month. A different time period might be applied upon selecting the countdown timer duration, based on the current weekday or the exact date within the month or the year. A different time period may be set for each injection device. The time period for an injection device may be recorded on the injection device and may be read by the device sensor. The time period for a type of injection device may be stored in the non-volatile memory.

The time period may be 1 or 2 days, and the display may be configured to show the number of hours until the scheduled dosing time is due. Similarly, for a time period on the order of a number of hours, the display may show a number of minutes.

A time period may be fixed for all injection devices. A predetermined time period may be stored in the non-volatile memory. Alternatively, a timer duration switch may be configured to select between any two time periods. For example, a first switch position may correspond to a time period of 7 days and a second switch position may correspond to a time period of 14 days. Alternatively, the timer duration switch may be a multi-positional switch, for example, a rotary switch or a dial. The time period may be set in conjunction with the display, wherein a first user input causes the display to show the current time period, and a second input is used to adjust the time period. A third input might be used to confirm the new settings.

Alternatively, the time period might be adjusted with a specific sequence of inputs using the reset button. For example, holding the reset button for a longer period of time, e.g. longer than 5 seconds, may initiate a "time period adjustment mode". The display may show the current timer duration, e.g. the display may show "14" to indicate 14 days. In this mode, pushing the reset button again for less than 5 seconds may increase the period incrementally. For example, a single button push may add 1 day, and the displayed value is changed accordingly. In this way, the user can adjust the period up to a predefined maximum value, e.g. "28". If the user pushes another time, then the time period may be dropped to a predefined minimum value, e.g. "14". If the user again holds the reset button for a longer period of time, e.g. longer than 5 seconds, the currently displayed value may be stored as the new time period and the normal operation is resumed. Alternatively, the value may be stored and normal operation resumed after a predetermined period with no input, e.g. after 10 seconds.

In some cases, the processor arrangement may not remove a redundant countdown timer. The countdown timer for a type of injection device may be maintained by the processor arrangement if the packaging assembly no longer contains an injection device of the corresponding type. A certain device type may be removed from the packaging assembly and later replaced with the same countdown timer. The processor arrangement may suppress an alert if the packaging assembly no longer contains an injection device of the corresponding device type when the countdown timer expires. Alternatively, the processor arrangement may output an alert. The processor arrangement may output a message to indicate a certain device type which is not contained in the packaging assembly.

The door timer and reset timer may operate on any suitable timeframe. For example, the user interface may enter the partial sleep mode if the fridge door is open for 10 minutes or 15 minutes. The reset button may be configured to reset the countdown timer if pressed for 1 second or up to 5 seconds.

The display may comprise more than 2 LED arrays, to accommodate larger numbers and messages, or more be a single LED array only. Alternatively, the display may comprise any form of electronic display suitable for displaying a number and/or a message, for example, the display may be an array of LED pixels, an LCD or e-paper screen, or a split-flap display. The display may be a display which is capable of displaying pseudo-3D images or video, e.g. a lenticular display. The display may be arranged in a peripheral module which is separate from the case. The display module may be connected to electrics system with a wired or wireless connection. The electronics system may comprise any display driver which is suitable for chosen display.

The display may be configured to provide further status information, or more detail, in the form of text messages on the display. For example, the display may provide a visual reminder that the scheduled dosing time is due by showing a reminder message in addition to, or instead of, flashing the number 00. The output of the number 00 is an example of a reminder message. The display may be controlled to show the number of injection devices remaining in the packaging assembly. The processor arrangement may be configured to determine the number of injection devices according to an input from the sensor array. Alternatively, the processor arrangement may be configured to monitor the number of times that a scheduled dosing time has passed. The display may be controlled to show a notification message when the packaging assembly is empty.

The display might be used to display a short sequence of pictures or a video, in 2D or in 3D, to show the correct usage or application of the injection device. The display may show any other useful information or advice connected to the therapy or the daily life of the patient.

The display may be controlled to display a warm-up time period when an injection device is removed from the packaging assembly. The display may be controlled in conjunction with the sensor array. When the scheduled dosing time for an injection device is due, the sensor array may be operated to detect the removal of the injection device. The display may display the warm-up time period when the sensor array detects the removal of the injection device. The warm-up time period represents the recommend time required for the injection device to reach room temperature. The processor arrangement may perform a timing operation based on the warm-up time period.

The processor arrangement may be configured to deactivate the display of the user interface if the lid of the case is closed. The processor arrangement may activate the LED array based on the fridge open sensor, to indicate to the user that the status of the packaging assembly is normal, when the number of days remaining is greater than one, whether the lid is closed or not. The user may open the lid to activate the display and show the number of days if required. When the scheduled dosing time is due, the processor arrangement may activate both the LED array and the display to flash, to provide a visual reminder, whether the lid is open or not.

The LED array may include a plurality of LEDs for each of the plurality of openings or one LED per opening. For example, the LED array may include four, five or six LEDs per opening, in order to provide a greater variety of status information. Alternatively, two or three of the LEDs for each opening may be replaced by a single two-colour or three-colour LED. Alternatively, any other form of notification light or visual output transducer may be used in place of the LED. Alternatively, the processor arrangement may flash or blink one of the plurality of LEDs, while the remaining LEDs are off or illuminated continuously. A different LED may be controlled to blink each time, to guide the user to the next injection device for use. One LED may be flashed in a different colour. The processor arrangement may control a number of LEDs according to the number of injection devices remaining in the packaging assembly.

The speaker may be any suitable form of audio output transducer, for example, an electro-acoustic transducer, a piezoelectric buzzer, a moving diaphragm speaker, or a mechanical bell. A vibrating alert may be used instead of or in addition to the audio output transducer. The speaker may output a different alert output, according to the type of device. For example, the speaker may vary the periodicity of an intermittent tone, or the frequency of the tone, or may output a pre-defined tone sequence e.g. a 3-tone sequence. Alternatively, the speaker may be configured to reproduce a digital audio file stored in the non-volatile memory. The reproduced digital audio file may be up to 6 seconds long or, alternatively, may be longer than 6 seconds.

A unique or individual alert may be used for each device type or, for example, to distinguish between alerts for different users of the packaging assembly. Audio alerts may be customisable by the user. In addition to an audio alert, the audio output of the speaker may be used to improve usability in other ways. For example, an audio output may indicate when an injection device is detected by the sensor array. A different audio output may be used according to whether the injection device is being inserted or removed.

The fridge open sensor may comprise a phototransistor or, alternatively, a photoresistor or photodiode. Alternatively, the fridge open sensor may comprise a mechanical switch. The fridge open sensor may be located externally from the case and may be positioned at a hinge or frame of the fridge door. The fridge open sensor may be a mechanical switch which is arranged to be pressed by the fridge door in a closed position.

The sensor array may be mounted on the panel, on a single PCB with the components of the electronics system. Alternatively, the sensor array may be mounted on a separate PCB. The sensor array may be positioned at the rear of the case, or internally on the upper or lower wall. A plurality of device sensors may be provided for each of the injection devices. The sensor array may alternatively comprise only a single device sensor. A single device sensor may activate and detect a plurality of device tags. The device sensor may determine the location of each device tag. Alternatively, a single device sensor may be externally positioned on the case, and the user may present each injection device to the device sensor before placing the injection device into the case. The device tag may be located at any point along the length of the injection device, or at either end thereof. The device tag may be located at the proximal end of the injection device, to increase a separation from the sensor array when the injection device is located in the opening. Alternatively, the device tag may be located at the distal end of the injection device, such that the sensor array can scan the device tag when the injection device is located in the opening.

Alternative device sensors may include optical sensors. Optical device tags such as, for example, barcodes or QR codes, may be provided on the plurality of injection devices. Alternatively, optical sensors may determine a colour or visual marking on an injection device to determine the type of injection device. In some embodiments, an optical sensor detects the presence of an injection device without receiving further device information. A device sensor may be implemented with a mechanical switch arranged to be pressed by an injection device when placed in the opening. The processor arrangement may determine the number of injection devices, the location of the injection devices and generate a device index for each injection device based on the detected presence of the injection devices. An alternative processor arrangement may iterate the device index only if both the device type and expiry date of an injection device match those of another injection device.

Alternative countdown timer implementations include off-chip and on-chip state-based logic circuits with clock devices, and other forms will be apparent to the skilled person.

The PCB and components of the electronics system may be sealed for protection. For example, the PCB may be coated on each side with a water resistant lacquer or another suitable coating. The electronics system may be coated for protection from moisture or humidity in the interior of a household fridge.

The packaging assembly may include a greater or smaller number of batteries, according to the power requirements of the electronics system. For example, the packaging assembly may include a single battery power pack. The battery or batteries may be removable and replaceable, or may be fixed within the case of the packaging assembly. Alternatively, the packaging assembly may be adapted for a mains power supply, or any alternative power supply.

The term "device type" is used to describe the physical sum of a drug container with a given drug and a given drug concentration, and the mechanical/electronical object performing relevant steps of the drug injection into the patient. The device type may be represented by one field in the device table or alternatively, for example, by two or more dependent fields to define the device type e.g. by specifying any of the medicament, concentration and delivery method of the injection device.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary). The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyhepta-¬decanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine. Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosureinclude, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. A packaging assembly comprising:
   a case configured to at least partially contain a plurality of injection devices that are each configured to deliver a medicament;
   a processor arrangement disposed at least partially within the case and configured to initiate a countdown timer based on a dosing period between scheduled dosing times of different injections for at least one injection device of the plurality of injection devices; and
   an input device configured to reset the countdown timer upon being pressed by a user, wherein the processor arrangement is further configured to:
   initiate a reset timer for monitoring a period of time that the input device has been pressed by the user, and
   when the period of time that the input device has been pressed by the user exceeds a threshold time period, initiate a "time period adjustment mode" that permits the dosing period to be adjusted upon the input device being depressed again by the user.

2. The packaging assembly of claim 1, wherein the threshold time period is 5 seconds.

3. The packaging assembly of claim 1, wherein in the "time period adjustment mode," the processor is configured to increase a timer duration incrementally upon the input device being pressed again for less than the threshold time period.

4. The packaging assembly of claim 1, wherein the period of time is a first period of time, and wherein in the "time period adjustment mode," the processor is configured to save a timer duration upon the input device being pressed again for a second period of time that exceeds the threshold time period.

5. The packaging assembly of claim 1, wherein the period of time is a first period of time, and wherein the processor arrangement is configured to reset the countdown timer when the input device is pressed for a second period of time that does not exceed the threshold time period.

6. The packaging assembly of claim 1, further comprising at least one device sensor that is configured to output a signal when one or more injection devices of the plurality of injection devices are located in the packaging assembly.

7. The packaging assembly of claim 6, wherein the at least one device sensor is configured to detect injection information relating to the one or more injection devices that have been detected.

8. The packaging assembly of claim 6, further comprising an injection information storage configured to retrieve injection information relating to the one or more injection devices that have been detected based on one or more respective detected identities.

9. The packaging system of claim 8, wherein the injection information comprises at least one of a dosing time period, a room temperature time period, or an expiry date.

10. The packaging assembly of claim 1, wherein the input device comprises a reset button.

11. The packaging assembly of claim 1, further comprising the at least one injection device of the plurality of injection devices received within the case, wherein the at least one injection device comprises a medicament.

12. A method of operating a packaging assembly, the packaging assembly comprising an input device and a case configured to at least partially contain a plurality of injection devices that are each configured to deliver a medicament, the method comprising:
   initiating, by a processor arrangement disposed at least partially within the case, a countdown timer based on a dosing period between scheduled dosing times of different injections for at least one injection device of the plurality of injection devices, wherein the input device is configured to reset the countdown timer upon being pressed by a user;
   initiating, by the processor arrangement, a reset timer for monitoring a period of time that the input device has been pressed by the user; and
   when the period of time that the input device has been pressed by the user exceeds a threshold time period, initiating, by the processor arrangement, a "time period adjustment mode" that permits the dosing period to be adjusted upon the input device being depressed again by the user.

13. The method of claim 12, further comprising displaying a current timer duration at a display.

14. The method of claim 13, further comprising:
- initiating, by the processor arrangement, a second reset timer to monitor the period of time that the input device has been pressed; and
- increasing the current timer duration incrementally when the second reset timer determines that the period of time that the input device has been pressed does not exceed the threshold time period.

15. The method of claim 14, wherein an incremental increase of the current timer duration comprises one day.

16. The method of claim 14, further comprising:
- initiating, by the processor arrangement, a third reset timer to monitor the period of time that the input device has been pressed;
- saving, by the processor arrangement, the current timer duration; and
- exiting, by the processor arrangement, the "time period adjustment mode" when the third reset timer determines that the period of time that the input device has been pressed exceeds the threshold time period.

17. The method of claim 12, wherein the packaging assembly further comprises the at least one injection device of the plurality of injection devices received within the case, and wherein the at least one injection device comprises a medicament.

* * * * *

UNITED STATES PATENT AND TRADEMARK OFFICE
CERTIFICATE OF CORRECTION

| | |
|---|---|
| PATENT NO. | : 11,724,021 B2 |
| APPLICATION NO. | : 17/088269 |
| DATED | : August 15, 2023 |
| INVENTOR(S) | : Hardy Kietzmann |

Page 1 of 1

It is certified that error appears in the above-identified patent and that said Letters Patent is hereby corrected as shown below:

In the Claims

In Column 44, Line 26, Claim 9, delete "system" and insert -- assembly --

Signed and Sealed this
Fourteenth Day of November, 2023

Katherine Kelly Vidal
*Director of the United States Patent and Trademark Office*